United States Patent
Nazhat et al.

(10) Patent No.: US 9,993,525 B2
(45) Date of Patent: Jun. 12, 2018

(54) BIOMATERIAL OF CHYMOTRYPTICALLY ISOLATED FRACTION OF FIBROIN IN A HYDROGEL

(75) Inventors: Showan N. Nazhat, Montreal (CA); Benedetto Marelli, Montreal (CA); Giuliano Freddi, Milan (IT); Antonio Alessandrino, Como (IT); Jake E. Barralet, Montreal (CA)

(73) Assignees: THE ROYAL INSTITUTION FOR THE ADVANCEMENT OF LEARNING, Montreal, QC; MCGILL UNIVERSITY, Montreal, QC ( * ) Notice: Subject to any disclaimer, the term of this patent is extended or adjusted under 35 U.S.C. 154(b) by 503 days.

(21) Appl. No.: 14/002,070

(22) PCT Filed: Feb. 28, 2012

(86) PCT No.: PCT/CA2012/000192
§ 371 (c)(1),
(2), (4) Date: Nov. 7, 2013

(87) PCT Pub. No.: WO2012/116439
PCT Pub. Date: Sep. 7, 2012

(65) Prior Publication Data
US 2014/0086874 A1 Mar. 27, 2014

Related U.S. Application Data

(60) Provisional application No. 61/447,375, filed on Feb. 28, 2011.

(51) Int. Cl.
| | |
|---|---|
| *C12N 5/00* | (2006.01) |
| *A61K 38/17* | (2006.01) |
| *C07K 14/435* | (2006.01) |
| *C07K 14/78* | (2006.01) |
| *C08J 3/075* | (2006.01) |
| *A61L 27/22* | (2006.01) |
| *A61L 27/24* | (2006.01) |
| *A61L 27/48* | (2006.01) |
| *A61L 27/52* | (2006.01) |
| *A61L 27/54* | (2006.01) |
| *C08H 1/00* | (2006.01) |
| *C08L 89/00* | (2006.01) |
| *C08L 89/06* | (2006.01) |
| *A61K 38/39* | (2006.01) |

(52) U.S. Cl.
CPC .......... *A61K 38/1767* (2013.01); *A61K 38/17* (2013.01); *A61K 38/39* (2013.01); *A61L 27/227* (2013.01); *A61L 27/24* (2013.01); *A61L 27/48* (2013.01); *A61L 27/52* (2013.01); *A61L 27/54* (2013.01); *C07K 14/43586* (2013.01); *C07K 14/78* (2013.01); *C08H 1/00* (2013.01); *C08J 3/075* (2013.01); *C08L 89/00* (2013.01); *C08L 89/06* (2013.01); *A61L 2400/06* (2013.01); *A61L 2430/02* (2013.01); *C08J 2389/00* (2013.01); *C08J 2489/00* (2013.01)

(58) Field of Classification Search
None
See application file for complete search history.

(56) References Cited

U.S. PATENT DOCUMENTS

| 7,727,542 B2 | 6/2010 | DiBenedetto et al. ....... 424/426 |
| 2004/0219630 A1 | 11/2004 | Tsubouchi |

FOREIGN PATENT DOCUMENTS

| WO | 03035124 A2 | 5/2003 |
| WO | WO 2006/003442 | 1/2006 |

OTHER PUBLICATIONS

Supplementary European Search Report with regard to EP12752652.3 dated Nov. 9, 2015.
Marelli, Benedetto et al., "Silk fibroin derived polypeptide-induced biomineralization of collagen", Biomaterials, Elsevier Science Publishers BV., Barking, GB, Sep. 2011, vol. 33, No. 1, pp. 102-108.
International Search Report issued in PCT Application No. PCT/CA2012/000192, dated Jun. 27, 2012.
International Preliminary Report on Patentability issued in PCT Application No. PCT/CA2012/000192, dated Sep. 3, 2013.
Lv et al., "Fibroin/collagen hybrid hydrogels with crosslinking method: preparation, properties and cytocompatibility", *J. Biomed Mater Res. A*, 84:198-2017, 2008.
Yamada et al., "Identification of fibroin-derived peptides enhancing the proliferation of cultured human skin fibroblasts", *Biomaterials*, 25:467-472, 2004.
Freddi, G. et al., "HPLC Fractionation of Cs Petides of Bombix Mori Silk Fibroin", Sericologia, 1989, 29(3), pp. 307-326.

*Primary Examiner* — Blaine Lankford
(74) *Attorney, Agent, or Firm* — BCF LLP

(57) ABSTRACT

A method for making a biomaterial comprising providing at least one polypeptide fraction chymotryptically isolated and extracted from fibroin, and adding the at least one extracted polypeptide fraction to a hydrogel precursor before gelling, wherein the at least one isolated and extracted polypeptide fraction is selected from a soluble fraction Cs, and a precipitated fraction Cp. A biomaterial comprising at least one of the isolated and extracted polypeptide fractions incorporated in a hydrogel or a hydrogel precursor. Use of the biomaterial for constructing, regenerating, repairing, replacing or augmenting soft or hard tissue; as an in vitro or in vivo construct; as a coating material; or as a cell, molecule or particle delivery medium. Use of the isolated and extracted polypeptide fraction Cs for promoting osteoinduction, osteoconduction or osteogenesis. Use of the isolated and extracted polypeptide fraction Cp for enhancing a mechanical compressive modulus of a material into which it is incorporated.

20 Claims, 12 Drawing Sheets

Scale bars=10 mm

Scale bars= 10 mm

Scale bar = 100 micron

BIOMATERIAL OF CHYMOTRYPTICALLY ISOLATED FRACTION OF FIBROIN IN A HYDROGEL

CROSS-REFERENCE TO RELATED APPLICATIONS

This application is a national phase application under 35 U.S.C. § 371 of International Application No. PCT/CA2012/000192 filed 28 Feb. 2012, which claims priority to U.S. Provisional Application No. 61/447,375 filed 28 Feb. 2011. The entire contents of each of the above-referenced disclosures is specifically incorporated herein by reference without disclaimer.

FIELD OF THE INVENTION

This invention relates generally to a biomaterial, a method for making the biomaterial, and uses of the same. Specifically, but not exclusively, the invention relates to biomaterials based on hydrogels, such as collagen, and polypeptides derived from fibroin.

BACKGROUND OF THE INVENTION

There is an ever increasing need for new biomaterials for the repair, replacement, construction or augmentation of hard and soft tissues in response to degenerative diseases, other diseases and conditions, trauma and cosmetic treatments. In particular, there is a need for biomaterials which are bioactive, and may be biodegradable, and possess appropriate mechanical and physical properties for a specific application. Depending on the application, biomaterials which are injectable or those with three-dimensional porous structures (i.e. scaffolds) for inducing cell invasion, attachment and proliferation may be required.

Biomaterials based on hydrogels are known. For example, collagenous hydrogels, such as type I collagen, have excellent biological behaviour, can form physiologically relevant scaffolds and can be injectable. However, collagenous materials have low strength and are therefore unsuitable for many applications. Also, most collagenous materials are rapidly and unpredictably reabsorbed by the body when implanted and also undergo significant cell contraction under physiological conditions.

Biomaterials based on mineralized collagen are particularly attractive for the repair, replacement, construction or augmentation of hard tissues, e.g., bone, as collagen forms the organic component of bone. Existing methods for mineralizing collagen require the processing of the collagen under conditions outside of physiological conditions in terms of pH, temperature, and high concentrations of minerals. As these mineralizing conditions cannot be recreated in the body, collagen must be mineralized before implantation and must therefore be implanted. These materials are also unable to support live cells during mineralization. An injectable mineralizable biomaterial based on collagen does not exist. Like unmineralized collagen, mineralized collagen also suffers from unpredictable reabsorption properties, and cell induced contraction.

Therefore, it is desired to provide an improved biomaterial, and method for making the biomaterial, for tissue construction, repair, replacement or augmentation in order to overcome or reduce at least some of the above described problems.

SUMMARY OF THE INVENTION

The aspects and embodiments of the present invention reduce, alleviate or overcome the aforesaid disadvantages, difficulties and deficiencies of the prior art by providing a novel biomaterial based on a hydrogel or a hydrogel precursor, such as collagen, collagen solution or other collagenous material, and incorporating isolated and extracted polypeptide fractions of fibroin.

Surprisingly, the inventors have discovered that a soluble polypeptide fraction (Cs) obtained by α-chymotrypsin digestion of the fibroin and extracted from the digested fibroin has mineralizing properties under physiological conditions when used alone and when incorporated into a biomaterial such as a hydrogel or a hydrogel precursor. The inventors have also surprisingly discovered that a precipitate polypeptide fraction (Cp) obtained by α-chymotrypsin digestion of the fibroin and extracted from the digested fibroin can enhance the mechanical properties of a material into which it is incorporated. It has been discovered that the extracted Cs and Cp fractions can be incorporated alone and in combination into a hydrogel or a hydrogel precursor to tailor the properties of the resultant biomaterial.

According to a first aspect of the invention, there is provided a biomaterial comprising at least one isolated and extracted polypeptide fraction of fibroin incorporated in a hydrogel or a hydrogel precursor, wherein the at least one isolated and extracted polypeptide fraction is chymotryptically isolated, and is selected from a soluble fraction Cs, a precipitated fraction Cp, or a combination of the Cs and Cp fractions.

In other words, a first aspect is directed to a biomaterial comprising a hydrogel or a hydrogel precursor including fibroin derived polypeptides which have been isolated from the fibroin by chymotryptic digestion and extracted from the digested fibroin. By 'incorporated' is meant linking, or the potential of linking, by chemical or physical attractions or joining for example by enzymatic action or the like, between the extracted polypeptide and the hydrogel or hydrogel precursor. Therefore, the invention encompasses biomaterials before, during and after gelation of the hydrogel. By isolated and extracted polypeptide fraction is meant that the polypeptide fraction has been isolated from fibroin and removed or separated from other isolated or non-isolated components of the fibroin.

Preferably, the fibroins originate from silkworms (class Insecta, order Lepidoptera, family Bombycidae (genus *Bombyx*, species *Bombyx mori, Bombyx mandarina*) and Satrurnidae (genus *Antheraea, Samia*, etc.), spider silk (silk produced by arthropods belonging to the class Arachnida, order Araneae), fibres within the keratin family or any other natural fibre.

α-Chymotrypsin digestion of fibroin results in the isolation of the hydrophilic polypeptide fraction (Cs) comprising negatively charged amino-acidic sequences, and the hydrophobic fraction (Cp) comprising apolar fragments. The Cs fraction is water soluble (Cs) and comprises polypeptides belonging to the amorphous regions of the fibroin. The molecular weight of the Cs fraction peptides ranges from 2 to 10 kDa. Cs contains the amino acids Asp, Ser, Glu, Gly, His, Arg, Thr, Ala, Pro, Tyr, Val, Met, Lys, Ile, Leu, and Phe. The Cp fraction is formed by the most hydrophobic peptides mainly comprising the repetitive -(Ala-Gly)$_n$- sequences characteristic of the crystalline regions of the fibre. Cp contains the amino acids Asp, Ser, Glu, Gly, Arg, Thr, Ala, Pro, Tyr, Val, Lys, Ile, Leu, and Phe.

The isolated Cp fraction can be extracted from the digested fibroin solution by centrifuging the digested fibroin solution, or any other suitable method of extracting the Cp fraction from the digested fibroin solution. The isolated Cs fraction can be extracted by freeze drying the digested fibroin solution once the Cp fraction has been removed, or by any other suitable method of extracting the Cs fraction from the digested fibroin solution. The extracted Cp and Cs fractions can be incorporated separately or together in different amounts in the hydrogel or hydrogel precursor to tailor the properties of the biomaterial. The extracted Cp and Cs fractions can be in powder, liquid or any other suitable form.

The inventors have demonstrated herein that the isolated and extracted Cs fraction of fibroin has mineralizing properties in both osseous and non-osseous conditions. Mineralization of collagen is the formation of an inorganic phase within the collagenous matrix, where the inorganic phase can include calcium phosphate, calcium carbonates, calcium oxalates, silicate species, etc. . . . . Mineralization can be an indicator of bone formation. The mineralizing effect of the extracted Cs fraction alone was found to be more enhanced than that of the undigested form of fibroin. The extracted Cs fraction has also demonstrated herein osteoinductive properties. Based on these demonstrated mineralization and osteoinductive properties, it is thought that the incorporation of the extracted Cs fraction in a hydrogel or hydrogel precursor can enhance the bone forming ability of the biomaterial such as by osteogenesis and osteoconduction. Therefore, the extracted Cs fraction whether incorporated in a hydrogel, a hydrogel precursor or any other biomaterial, could be useful for hard tissue applications where the repair, regeneration, augmentation, construction or replacement of bone or teeth is required.

The inventors have also demonstrated herein that the isolated and extracted Cp fraction of fibroin can enhance the mechanical compressive modulus and strain of a material into which it is incorporated. Therefore, the integration of the extracted Cp fraction in a hydrogel or hydrogel precursor can lead to the mechanical reinforcement of the resultant biomaterial which can slow its reabsorption in vivo. Control of the mechanical properties of the biomaterial may also direct phenotype and differentiation of stem cells or other cells seeded in the biomaterial. Cp could also reduce the vulnerability of a hydrogel such as collagen to cell-induced contractile behaviour. Therefore, the combination of extracted Cp polypeptide fractions and a hydrogel could be useful for adapting the mechanical properties of a hydrogel for soft tissue applications. A biomaterial based on this combination would be particularly useful for non-mineralizing cell delivery. Cp alone is considered to stabilize a matrix.

Advantageously, fibroin is a widely available material and the isolated and extracted polypeptide fractions, Cs and Cp, can be easily, quickly and cheaply obtained from fibroin by known methods, such as by chymotryptic digestion of the fibroin. The polypeptides thus obtained are biocompatible, easy to sterilize, to process and to be maintained.

Instead of obtaining the extracted polypeptide fraction through a top-down approach of chymotryptic digestion, the Cs and Cp fractions as defined herein can be synthesized through a bottom-up approach.

The biomaterial can be in the form of an injectable system. In this case, the isolated and extracted polypeptide fraction is incorporated in a hydrogel precursor, or a hydrogel having a viscosity suitable for injection in a human or animal body. In other words the biomaterial is flowable or substantially liquid. By substantially liquid is meant that the biomaterial has a suitable viscosity to allow it to be delivered to a site of treatment in a patient (such as by injection or the like). The biomaterial may become more viscous (e.g. gel) in situ due to a change in temperature, pH, ionic environment or the like. Gelling in the biomaterial can be initiated just before injecting into a host site, for example by adjusting the temperature, pH or ionic environment of the biomaterial. Advantageously, when in injectable form, the biomaterial can be delivered to awkward to reach sites within a host, can also carry cells, drugs and other agents, can gel in situ and so can fill awkward shapes, can allow for direct contact between cells in the biomaterial and host tissue, and can reduce the need for invasive surgery. Injectable hydrogels with biodegradability can provide an effective and homogeneous encapsulation of drugs/cells, and convenient in vivo surgical operation in a minimally invasive way, causing smaller scar size and less pain for patients. Gelation and biodegradation of the biomaterial are two factors which affect cell fate or drug delivery from the biomaterial.

In one embodiment, there is provided an injectable biomaterial based on collagen which can mineralize in vivo, the injectable biomaterial comprising a chymotryptically isolated and extracted Cs polypeptide fraction in a collagenous material. The collagenous material is a collagen solution. The extracted Cs polypeptide fraction can be in the form of particles and be placed in suspension in the collagen solution.

Alternatively, the biomaterial is substantially solid or substantially gelled and implantable in a human or animal body. The biomaterial comprises a three-dimensional scaffold or matrix. The implantable biomaterial can be a flat or a rolled sheet, sponge or film. The biomaterial can be any other shape such as a tube, block, ring or fibre. The biomaterial may be shaped by moulding during gelling or cutting after gelling, for example. The biomaterial may also be a multi-layered construct and may form part of a multi-layered construct.

Preferably, the extracted polypeptide fractions are added to the hydrogel or the hydrogel precursor before the hydrogel has gelled. The biomaterial can also be a dense hydrogel, such as a dense collagen hydrogel, incorporating the isolated and extracted polypeptide fraction(s).

Preferably, the hydrogel or hydrogel precursor is based on type I collagen. Advantageously, this is resorbable and biocompatible and is a major component of bone. The hydrogel or hydrogel precursor can also be any collagenous material from any suitable source such as rat tail tendon and bovine dermis (for type I collagen) and cartilage for type II collagen. The hydrogel or hydrogel precursor may have natural or synthetic sources, and may include fibrin, chitosan, hylauronic acid, alginates, gelatin, heparin, chondroitin sulfate, etc. The hydrogel or hydrogel precursor may be resorbable. Use of naturally derived materials in a biomaterial is advantageous from a biocompatibility point of view. Although the examples herein use collagen-based materials as the hydrogel and the hydrogel precursor, it is believed that a similar effect would be obtained with hydrogels other than collagen.

Advantageously, when the hydrogel or hydrogel precursor is collagen or a collagen solution, the resultant biomaterial retains the beneficial properties of the collagenous material and benefits from the properties of the incorporated extracted polypeptide fraction(s). In the embodiments where the biomaterial comprises isolated and extracted Cs and Cp particles in a collagenous material, the gelled biomaterial comprises a matrix of collagen fibrils having particles or agglomerates of particles of Cs or Cp attached to the fibrils.

Preferably, the at least one isolated and extracted polypeptide fraction is incorporated in the hydrogel or hydrogel precursor in the range of about 0.1 to about 50 dry wt %, preferably about 0.1 to about 30 dry wt %, more preferably about 5 to about 10 dry wt %, most preferably about 10 dry wt %. Preferably, a Cs content is less than or equal to about 30 dry wt % Cs in a collagen hydrogel or collagen hydrogel precursor. These ranges of isolated and extracted polypeptide fraction incorporation can produce biomaterials with a range of properties (biological, mechanical, chemical and the like). Therefore, an appropriate content of polypeptide fraction can be utilized according to the intended use of the biomaterial.

The biomaterial may additionally include cells, drug molecules, therapeutic agents, particles, bioactive agents, or the like, without adversely altering the viability or the state of these substances. The cells, drug molecules, therapeutic agents, particles, bioactive agents, or the like can be distributed interstitially within the biomaterial in any arrangement, such as homogeneously or in defined zones or layers. Examples of bioactive agents include bioactive glass, soluble glass, resorbable calcium phosphate, hydroxyapatite, glass-ceramics, to name a few. The cells may include those involved in hard and soft tissue generation, regeneration, repair and maintenance, for example mesenchymal stem cells, bone marrow stem cell, osteoblasts, preosteoblasts, fibroblasts, muscle cells and chondrocytes, and the like. Therapeutic agents can include hormones, antimicrobials, anti-rejection agents and the like. The drugs can be any molecules for disease, condition or symptom treatment or control, anti-inflammatory, growth factors, vesicle for release of ions, release of gas, release of nutrients and enzymes. In this way, the biomaterial may be used as a substance carrier or as a delivery vehicle, such as for controlled release of drugs or therapeutic agents.

The cells, drug molecules, therapeutic agents, particles, bioactive agents, or the like can be added to the biomaterial before or after gelation of the hydrogel precursor to form the hydrogel as advantageously, gelling of a collagen solution including the extracted polypeptide fractions can occur under physiologic conditions or at least conditions which are not detrimental to cells, drug molecules, therapeutic agents, particles, bioactive agents, or the like. They can be added to the hydrogel precursor and be delivered to a host site by injection or the like. Advantageously, it has been found that when extracted Cs particles are present in the biomaterial, stem cells are steered to bone cells. In other words, the extracted Cs particles are osteoinductive.

In one embodiment, the biomaterial comprises collagen or a collagen solution including isolated and extracted Cs particles. This can be considered as a 'collagen biomaterial'. Advantageously, this biomaterial can mineralize under physiologic conditions in vitro and in vivo (see Examples) in a relatively short time frame. As the biomaterial is based on collagenous materials, it is inherently biocompatible. The biomaterial is porous enough to allow cell seeding and penetration, as well as oxygen and nutrient transport to the seeded cells. In vivo, the biomaterial can be reabsorbed in a period of time compatible with the tissue repair process. It mimics the extracellular structure of tissues due to its collagenous material base. By varying the amount of the extracted Cs particles, as well as adding extracted Cp particles to the biomaterial, the properties of the biomaterial can be tailored for many different tissue types and uses as stated above. It can be delivered in vivo in liquid form and gel in situ. The biomaterial is non-immunogenic.

Unlike prior art systems, the biomaterial of the present invention when based on collagenous materials maintains the original biological, chemical and physical properties of the collagenous material due to its gelling or fibrillogenesis under physiologic conditions. However, the disadvantageous properties of the collagenous material are overcome or minimized by the incorporation of isolated and extracted fibroin derived polypeptide fractions Cs, Cp, or Cs and Cp.

In the present invention, the use of fibroin derived polypeptides and their hybridization with a collagenous material or a hydrogel provides a novel biomaterial with improved properties. This new biomaterial combines the advantages of extracted polypeptides with the advantageous and beneficial properties of collagenous materials. Surprisingly, the properties of the resultant biomaterial are beyond those of the individual components making up the biomaterial. The extracted Cs and Cp polypeptide particles are not capable of making hydrogel systems on their own. Silk fibroin can form a hydrogel but requires non-physiologic conditions and so cannot support viable cells. Collagen cannot mineralize under physiologic conditions.

Silk fibroin is known for its bioactivity and for its mechanical and biological properties. However, so far in the prior art, its processing in gel has required the use of non-physiologic conditions and long time periods (from one day up to several weeks). At 37° C. and pH 7.4 fibroin sol-gel transition takes days to weeks and consequently makes it impossible to incorporate cells and maintain them alive in the gel. Adding salts at concentrations above physiological (i.e. cytotoxic) levels does not significantly alter the gelation kinetics but compromises cell incorporation. Lowering pH (pH<5) or increasing temperature (>60° C.) could reduce the gelation time to a few hours but these conditions alter cell function and affect cell viability. Alternatively, pre-sonication of fibroin solution increases gelation kinetics within a physiological environment, but does not guarantee the achievement of a nanofibrillar structure highly suitable for biomaterials purposes. The incorporation in a hydrogel of isolated and extracted fibroin derived polypeptides has never been proposed, to the inventors knowledge. The specific properties of such isolated and extracted polypeptide fractions have also never previously been identified.

Suitable applications or uses for the biomaterial of the present invention include tissue engineering, soft and hard tissue construction, repair, regeneration and/or augmentation. Regenerative medicine is another use such as delivery of stem cells in cardiomyosplasty, wound healing, diabetes and neurodegenerative diseases, to name a few. Hard tissue can include bone and teeth. Soft tissue can include skin, muscles, tendons, ligaments, cartilage, cornea, periodontal tissue, vessels, bladder, and airway tissues such as lung, and the like. Other applications include as in vitro or in vivo constructs; as a coating material; as a two or three dimensional cell culturing substrate; as a delivery vehicle for cells, drugs and other agents; for cosmetic purposes such as anti-ageing treatments or face reconstruction.

The invention also relates to use of the biomaterial as defined above as a medical device or implant, or included in a medical device or implant. Advantageously, the implants may be tissue equivalent implants. The biomaterial can be used in a therapeutically effective amount for alleviating or treating a bone, tooth or cartilage defect in a mammal. Therefore, the invention also includes a method of alleviating or treating a bone, tooth or a cartilage defect in a mammal comprising administering to said defect a therapeutically effective amount of a biomaterial as described herein. Use of the biomaterial as herein described in orthopaedics is also included. Also included is use of the biomaterial to at least partially fill a bone or tooth defect.

From another aspect, there is provided use of a biomaterial as defined above for constructing, repairing, replacing, regenerating or augmenting soft or hard tissue; as an in vitro or in vivo construct; as a coating material; or as a cell, molecule or particle delivery medium. One advantageous use of the biomaterial incorporating at least the extracted Cs polypeptide fraction is for promoting mineralization or bone formation including one or more of osteoconduction, osteoinduction, and osteogenesis.

From yet another aspect, there is provided a method for making a biomaterial comprising providing at least one polypeptide fraction chymotryptically isolated and extracted from fibroin, and adding the at least one extracted polypeptide fraction to a hydrogel precursor before gelling, wherein the at least one isolated and extracted polypeptide fraction is selected from a soluble fraction Cs, a precipitated fraction Cp, or a combination of the Cs and Cp fractions. It will be understood that before gelling means before substantial gelling or polymerization has taken place. The gelling or polymerization process need not be complete.

The method can further comprise isolating the at least one polypeptide fraction from the fibroin by α-chymotrypsin digestion and extracting the at least one isolated polypeptide fraction from the digested fibroin. The hydrogel precursor can be a collagen solution, for example based on naturally derived Collagen Type I. Incorporating the at least one isolated and extracted polypeptide fraction can comprise providing the extracted polypeptide fraction in particulate form and forming a suspension in the hydrogel precursor, such as in collagen solution.

The method can further comprise at least partially gelling the hydrogel precursor. The hydrogel precursor can self-gel or require processing steps. The at least partial gelling of a collagen solution hydrogel precursor can be initiated by adjusting the pH to about 5.5 to about 9.5. The biomaterial can be injected when ungelled or partially gelled, or implanted when at least partially gelled. The biomaterial can be made more dense by extracting at least some fluid by a compression or a consolidation method. The biomaterial can be moulded or shaped into any suitable form such as a block, sheet, fibre, tube, ring, roll, to name a few.

Advantageously, cells, drug molecules, therapeutic agents, particles or bioactive agents can be added to the hydrogel precursor before gelling or to the biomaterial. Advantageously, these substances are added to the hydrogel precursor before gelation. As gelation occurs under physiologic conditions, cell viability may be maintained and no adverse effect of gelling on the added substances.

Preferably, the hydrogel precursor is a collagen solution and the at least one extracted polypeptide fraction is incorporated in the biomaterial in the range of about 0.1 to about 50 dry wt %, preferably about 0.1 to about 30 dry wt %, more preferably about 5 to about 10 dry wt %, most preferably about 10 dry wt %. Preferably, a Cs content is less than or equal to about 30 dry wt % Cs in the biomaterial.

The method includes providing the isolated and extracted Cs and Cp fractions in different or same amounts. The method also includes adjusting these amounts to tailor the properties of the biomaterial.

In one embodiment, incorporating the extracted polypeptides comprises forming a suspension of the extracted polypeptide particles in a solution of collagenous material and leaving them to interact, prior to gelation. The method can further comprise gelling the polypeptide-collagenous material suspension to form a gel by adjusting the pH of the solution to about 5.5 to about 9.5, preferably pH 6 to 9, for gelation such as by adding a base. The suspension may also be incubated at a suitable temperature such as 37° C. for gelation. Polypeptide particles, culture medium, collagen solution, and a base may be added together in any order.

Surprisingly, without being bound to theory, the polypeptides and the collagenous material are thought to start interacting when the pH of the suspension is more than about 3, by the formation of electrostatic bonds, for example. Thereafter, during gelling, they form physical and chemical bonds. The gelation occurs in a time window of about 30 minutes at about 37° C. and at a pH of between about 5.5 to about 9.5, preferably, about 6 to 9.

The method may also further comprise densification of the hydrogel such as by removing at least some of the water content. In one embodiment, this is performed by plastic compression as described in WO2006003442, the contents of which are herein incorporated by reference, which includes applying a compressive load between 0.1 to 100 kPa, preferably about 1 kPa, over a 1 to 15 minute period, preferably 5 minutes. By using the dense collagen production method, a mineralizable dense collagen hydrogel biomaterial can be obtained quickly, in terms of hours as opposed to alternative methods of collagen gelation and densification which require cell action and can take weeks with unreliable results.

The method can further include processing the biomaterial before or after gelling or densification using UV light, radiations, enzymes (e.g. Transglutaminase, Tyrosinase), crosslinking agents, mechanical solicitation, pH, temperature and pressure alterations.

Alternative or additional method steps may also be included to link the extracted Cp and Cs fractions to the hydrogel, for example by enzymatic, chemico-physical and mechanical processing of the biomaterial. For example, additional processing may include applying to the hydrogel or hydrogel precursor before, during or after its gelation: UV light, radiations, enzymes (e.g. Transglutaminase, Tyrosinase), crosslinking agents (e.g. aldehydes, carbodiimides, dehydrothermal treatment, acyl-azide based and cyanid based chemicals), mechanical solicitation, pH, temperature and pressure alterations, to post-process the materials and further increase the interaction and the bonds between collagen and the extracted polypeptide fractions.

The present invention also includes biomaterials made using the method described herein.

A further aspect of the invention includes the use of an isolated and extracted polypeptide fraction of fibroin for promoting osteoinduction, osteoconduction or osteogenesis (bone growth), minerlization, or as a physiologically active agent, wherein the polypeptide fraction is isolated by α-chymotrypsin digestion of the fibroin and contains the amino acids Asp, Ser, Glu, Gly, His, Arg, Thr, Ala, Pro, Tyr, Val, Met, Lys, Ile, Leu, and Phe. This is the soluble fraction Cs. The inventors have shown that the isolated and extracted Cs polypeptide fraction has a greater mineralization effect than fibroin (comprising non-isolated polypeptide fractions) alone. Therefore, the isolated and extracted Cs fraction can be used within or in conjunction with any biomaterial or matrix to enhance mineralization. Further uses are in orthopaedics, to alleviate, treat or partially fill a bone or tooth defect in a mammal.

A yet further aspect is the use of an isolated and extracted polypeptide fraction of fibroin for enhancing a mechanical compressive modulus of a material into which it is incorporated or for stabilizing a matrix, wherein the polypeptide fraction is isolated by α-chymotrypsin digestion of the fibroin and contains the amino acids Asp, Ser, Glu, Gly, Arg, Thr, Ala, Pro, Tyr, Val, Lys, Ile, Leu, and Phe. Further uses include as a matrix stabilizer when incorporated in a matrix forming material.

In both aspects, the isolated and extracted polypeptide fraction can be incorporated in a biomaterial which can be a hydrogel or a hydrogel precursor, or any other suitable biomaterial. The biomaterial can be a collagenous material.

DEFINITIONS

The singular forms "a", "an" and "the" include corresponding plural references unless the context clearly dictates otherwise. As used herein, the term "comprising" is intended to mean that the list of elements following the word "comprising" are required or mandatory but that other elements are optional and may or may not be present. As used herein, the term "consisting of" is intended to mean including and limited to whatever follows the phrase "consisting of". Thus the phrase "consisting of" indicates that the listed elements are required or mandatory and that no other elements may be present.

As used herein, by "biomaterial" is meant a material that is biocompatible with a human or animal body when in contact with the body such as by implantation, injection or any other contact. It can be in liquid, gel or solid form.

As used herein, by "fibroins" is meant one or more constituents of silk fibre, filament or web which can be from different animal sources such as silk worm or spider.

As used herein, by "hydrogel" is meant any dispersion of molecules, fibres or particles within a liquid (e.g. water) in which the solid (from about 0.05% to about 50% solid) is the discontinuous phase and the liquid is the continuous phase. The molecules, fibres or particles are linked by physical and/or chemical interactions. Hydrogels can include collagens, alginates, hyaluranon, chitosan, fibrin, agarose, polyacrylamide, PEG (polyethylene glycol), PAA (polyacrylic acid), HEMA (hydroxy ethyl methacrylate) and the like. For example, a collagen hydrogel comprises a three-dimensional network of fibrils surrounded by interstitial fluid.

As used herein, by 'hydrogel precursor' is meant the form of the hydrogel before formation of the solid phase (e.g. before 'gelling' or 'self-assembly'). For example, a collagen hydrogel precursor is a collagen solution in which the fibrils have not yet polymerized and are in soluble monomer form.

As used herein, by "collagen" is meant any collagenous material dominated by collagen molecules capable of self assembly into collagen fibrils. Includes type I and type II collagen from any source. Collagenous material may be in a liquid or gel form.

BRIEF DESCRIPTION OF THE DRAWINGS

Further aspects and advantages of the present invention will become better understood with reference to the description in association with the following drawings, in which.

DETAILED DESCRIPTION OF THE INVENTION

Figure 1:
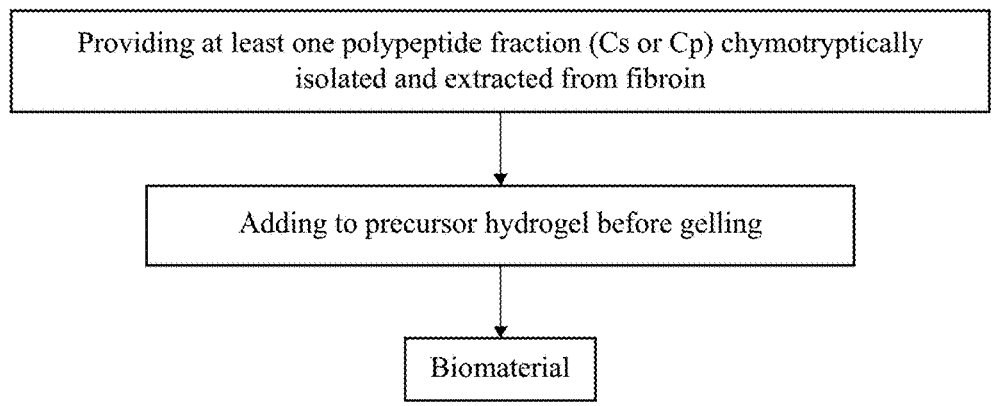
FIG. 1 is a schematic of an embodiment of a method of the invention to make a biomaterial.

This invention is not limited in its application to the details of construction and the arrangement of components set forth in the following description or illustrated in the drawings. The invention is capable of other embodiments and of being practiced or of being carried out in various ways.

A first aspect of the invention is to a method (FIG. 1) for making a biomaterial comprising providing at least one polypeptide fraction isolated and extracted from fibroin, and adding the at least one extracted polypeptide fraction to a hydrogel precursor before gelling. The at least one isolated and extracted polypeptide fraction is α-chymotryptically isolated and is a soluble fraction Cs, a precipitated fraction Cp, or a combination of the Cs and Cp fractions.

In a first embodiment of the method, the hydrogel precursor is a type I collagen solution and the at least one extracted polypeptide fraction is derived from Bombyx mori silk fibroins, although other hydrogel precursors and fibroin sources are possible. The polypeptides are isolated by digestion of silk fibroin fibers by α-chymotrypsin, resulting in the formation of a highly crystalline, apolar precipitate fraction (Cp) and an amorphous, negatively charged soluble fraction (Cs), in a manner known in the art. Specifically, the silk fibroin obtained by silk degumming is dissolved within a saturated LiBr aqueous solution, at 60° C., for 3 hours. The solution is filtered, dialyzed against water. α-chymotrypsin solution obtained by dissolving the enzyme in 10 mM Tris-HCl, 5 mM $CaCl_2$ is then added to the aqueous fibroin solution (enzyme concentration of 300 μg/ml). The so obtained solution is incubated at 37° C. for 24 hours. The precipitated Cp fraction is extracted by centrifugation of the solution, while Cs is extracted by freeze drying it, once Cp has been removed. Cs may also be maintained in solution, although it is more difficult to control its concentration in the hydrogel in this way.

In this embodiment, the extracted polypeptide particles (Cs alone, Cp alone, or Cs and Cp together) are mixed with a culture medium, a collagen solution, and a base before gelation of the collagen solution which incorporates the extracted polypeptides within the collagenous material. The extracted polypeptides, culture medium, collagen solution, and base may be mixed in any order. The suspension including the polypeptide particles and any of the other ingredients may be sonicated for homogenous dispersion of the polypeptide particles. Gelation is thought to occur within about half an hour of the base (NaOH) being added and the pH being adjusted to about pH 5.5 to about pH 9.5, and the temperature being about 37° C. (in situ conditions). The rate of gelation can be controlled by temperature. Vials of the collagen-polypeptide suspension can be kept refrigerated until needed. Differing amounts of the Cp and Cs polypeptide fractions may be used in order to tailor the properties of the resultant biomaterial.

In a second embodiment of the method, an implantable biomaterial based on collagen and extracted polypeptide fractions is made. This embodiment differs from the first embodiment in that the isolated and extracted polypeptide particles in a collagen suspension is gelled by incubating the suspension in a mould for about 15 minutes to about 24 hours, preferably about 25 minutes, at a temperature of about 0 to 37° C., preferably 37° C. The gelled biomaterial may also be consolidated to form a more dense ordered mesoscale structure. One way of doing this is by removing the liquid phase such as by applying an unconfined compressive load, or any other suitable method. However, the method is not limited to dense collagen gels and the collagenous material in the biomaterial can range from about 0.1% to about 40% collagen fibrillar density.

From another aspect, there is provided a biomaterial comprising at least one isolated and extracted polypeptide fraction of fibroin incorporated in a hydrogel or a hydrogel precursor, wherein the at least one isolated and extracted polypeptide fraction is chymotryptically isolated and selected from a soluble fraction Cs, a precipitated fraction Cp, or a combination of the Cs and Cp fractions.

In one embodiment, the polypeptides are derived from Bombyx mori silk fibroins. The hydrogel or hydrogel precursor is a collagenous material. The biomaterial is implantable and comprises a network of collagen fibrils incorporating the isolated and extracted Cs, Cp, or Cs and Cp particles. The Cs and/or Cp particles are attached to the fibrils of the collagen network.

In another embodiment, the biomaterial is injectable and has a suitable viscosity for being injected. The injectable biomaterial comprises a suspension of the isolated and extracted polypeptide particles, preferably in a collagen solution. Varying the amounts of Cs and/or Cp incorporated into the collagenous material varies the biological and mechanical properties of the resultant gelled biomaterial.

The invention is further illustrated by the following non-limiting examples.

EXAMPLES

Example 1

Dense Collagen Gels Incorporating Isolated and Extracted Cs or Cp Articles: Effect on Mineralization and Mechanical Properties (In Vitro)

Figure 2:
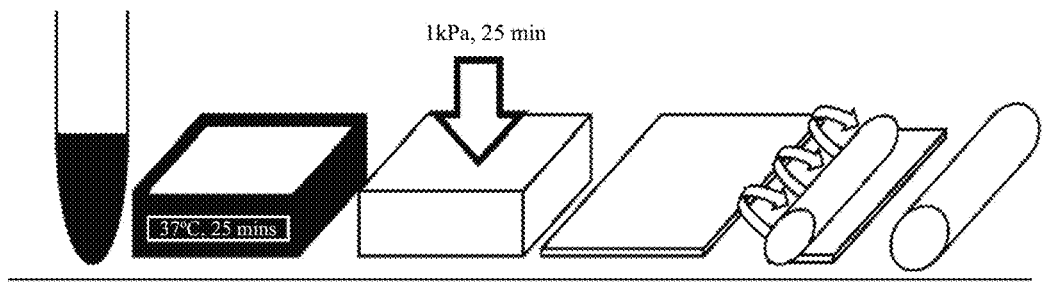
FIG. 2 is a schematic of another embodiment of the method of the invention (Example 1)

Dense collagen gels with differing amounts of isolated and extracted fibroin-derived polypeptide fractions (FDP)

were made according to an embodiment of the present invention, as illustrated in FIG. 2 and described below. The FDP were isolated by digestion of silk fibroin fibres from the *Bombyx mori* silkworm using α-chymotrypsin, resulting in the formation of a precipitated fraction (Cp) comprising highly crystalline apolar fragments and a soluble fraction (Cs) comprising amorphous, negatively charged amino-acidic sequences. Specifically, fibroin obtained by silk degumming was dissolved within a saturated LiBr aqueous solution, at 60° C. for 3 h. The solution was filtered and dialyzed against water. α-chymotrypsin solution obtained by dissolving the enzyme in 10 mM Tris-HCl, 5 mM $CaCl_2$ was then added to the aqueous fibroin solution (enzyme concentration of 300 μg/ml). The so obtained solution was incubated at 37° C. for 24 h. The precipitated Cp fraction was extracted by centrifugation of the solution, while the Cs fraction was extracted by freeze drying, once the Cp fraction had been removed. Both the extracted Cs and the Cp fractions were in powder/particulate form.

10 dry wt % Cp and 10 dry wt % Cs were then added to a collagen solution before gelation and densification of the collagen, to form the biomaterial. The required amount of the extracted FDP particles was added to a culture medium (DMEM 10x, D 2429, Sigma Aldrich) and sonicated for about 1 to about 10 minutes, preferably about 5 minutes. For a 10 dry wt % FDP particle content, 0.88 mg of extracted FDP particles were added to 4 ml of the culture medium. The collagen solution, an acidic tropocollagen solution (collagen hydrogel precursor) (type I collagen extracted by rat tail, 2.05 mg/ml, FirstLink) was added and the solution left for 0 minutes to 12 hours, preferably about 1 hour, at a temperature of about 0° C. to about 37° C., preferably room temperature, to allow the tropocollagen and the extracted FDP particles to interact to form a collagen-FDP particle suspension. In order to at least partially gel the collagen-FDP particle suspension, the pH was adjusted to about 5.5 to about 9.5 using a base (e.g. NaOH at PH 7.4). The final solution was incubated in a mould for about 15 minutes to 24 hours, preferably 25 minutes, at a temperature of about 0° C. to about 37° C., preferably about 37° C. to allow gelling of the collagen-FDP particles ('self-assembly'). It will be appreciated that the tropocollagen solution, culture medium, FDP and base may be added in any order to obtain the final collagen-FDP suspension. Also, the sonicating step is not essential but was preferred in order to obtain a homogenous dispersion of the FDP particles in the suspension and to avoid or minimize the formation of clusters. Furthermore, different relative concentrations of the ingredients may be used without departing from the scope of the invention, as will be apparent to those skilled in the art.

The resulting gelled biomaterial was then subjected to 'plastic compression' to form a dense gel. 'Plastic compression' has been described fully in WO2006003442, the contents of which are herein incorporated by reference. Briefly, the highly hydrated collagen-FDP gels were subjected to an unconfined compressive stress (plastically compressed) of 0.1 to 100 kPa, preferably about 1 kPa, over a 1 to 15 minute period, preferably 5 minutes, resulting in the expulsion of approximately 98% of the fluid content, and a corresponding 40-fold increase in collagen fibrillar density from 0.3 to 14%. This step therefore produces dense collagen constructs or scaffolds with controlled protein concentration and meso-scale structure, thus enhancing the mechanical characteristics of collagen hydrogels. The dense collagen-FDP sheet was then rolled to form a 'swiss roll' cylindrical structure for mechanical testing.

Figures 3, 4:
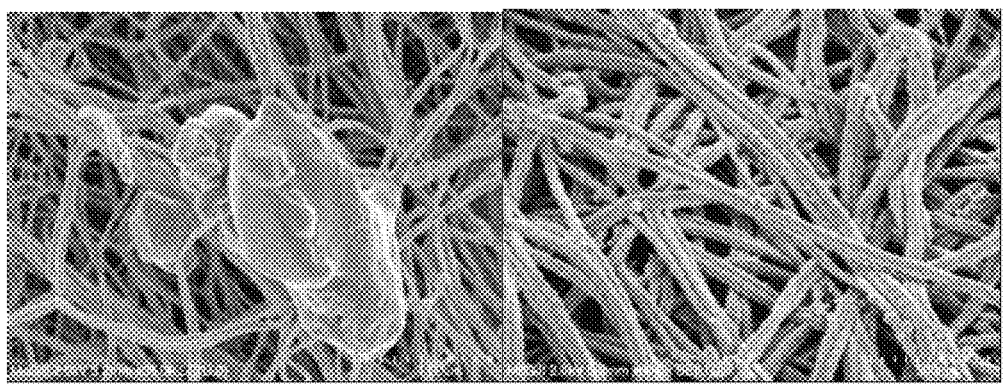
FIG. 3 is a SEM micrograph of an embodiment of a biomaterial of the present invention showing an isolated and extracted Cp polypeptide particle in a collagen gel framework (Example 1)
FIG. 4 is a SEM micrograph of an embodiment of a biomaterial of the present invention showing an isolated and extracted Cs polypeptide particle in a collagen gel framework (Example 1)

The resultant biomaterial was found to be in the form of a hydrogel having a collagenous framework hybridized (bonded, linked, conjugated) with extracted FDPs. FIGS. 3 and 4 illustrate embodiments of the biomaterial of the present invention having 10 dry wt % Cp and Cs, respectively. In FIG. 3, interaction and bonds between the collagen protein and the extracted Cp particles are evident from the interconnection between the collagen nanofibrils and the Cp particle. Surprisingly, the collagen nanofibrils were found to have extracted polypeptide Cp particles at their ends indicating the formation of bonds between the two, rather than electrostatic interaction only. Typical collagen banding shows that the integration of the extracted Cp before self-assembly (gelation) of the collagen does not alter the natural structure of collagen, when compared to neat collagen gels with no extracted FDP present. The same result was found for biomaterials having extracted Cs polypeptide fractions only (FIG. 4), where the submicrometric (nano) amorphous polypeptides were found homogenously distributed in the gel and linked to the collagen nanofibrils. Morphological and chemical characterization of the biomaterial showed that hybridization of collagen with the extracted FDPs occurred within 30 minutes of collagen gelation.

Figure 5:
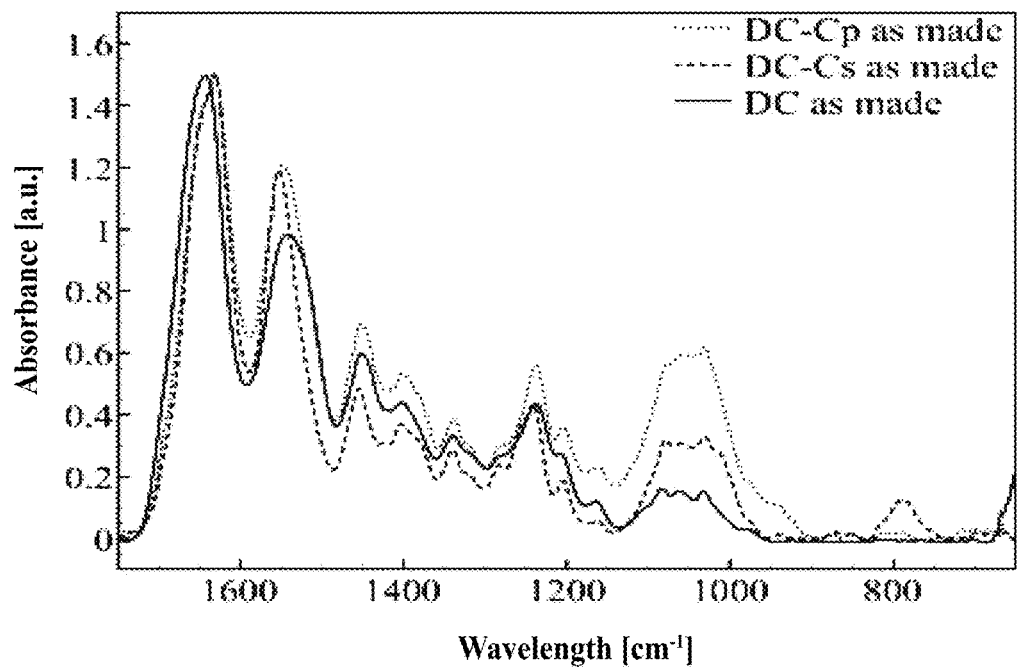
FIG. 5 is ATR-FTIR spectra of embodiments of the biomaterials of the present invention incorporating: (i) Cp polypeptides (DC-Cp), (ii) Cs polypeptides (DS-Cp), compared with a collagen control with no extracted polypeptides (DC) (Example 1)

The morphological analysis was corroborated by ATR-FTIR spectroscopy of the biomaterial including the isolated and extracted Cp and Cs polypeptide fractions, when compared to a collagen only control (FIG. 5). Modification of the three amide vibration (amide I at 1643 $cm^{-1}$, amide II at 1550 $cm^{-1}$ and amide III at 1243 $cm^{-1}$) and the different resonance of the amino acid side chains between 1150 and 800 $cm^{-1}$ were an indication of interaction between the collagen fibrils and the FDP.

Figure 6:
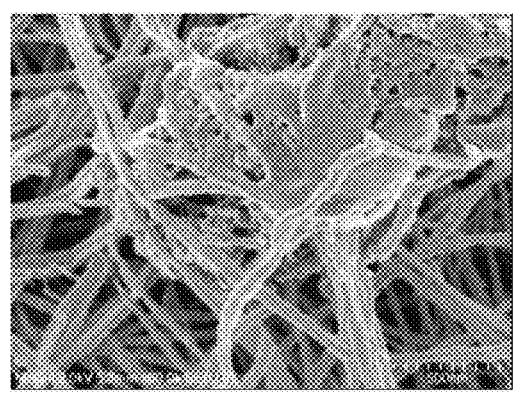
FIG. 6 is a SEM micrograph of an embodiment of the biomaterial of the present invention at day 7 in simulated body fluids, the biomaterial including 10 dry wt % isolated and extracted Cp particles in collagen (Example 1)

The mineralization behaviour of the biomaterials was assessed by placing samples of the compressed biomaterials in simulated body fluids (SBF) up to day 7. Neat collagen was used as a control. Differing the amount of the extracted Cp and Cs fractions in the biomaterial affected the mineralization activity of the biomaterials. Biomaterials with extracted Cp polypeptides only showed no statistically significant differences in their mineralization in SBF when compared to neat collagen. As can be seen in the SEM micrograph of FIG. 6, the extracted Cp particles remained integrated and bonded to the collagenous framework. No crystal formation was visible.

Figures 7, 8:
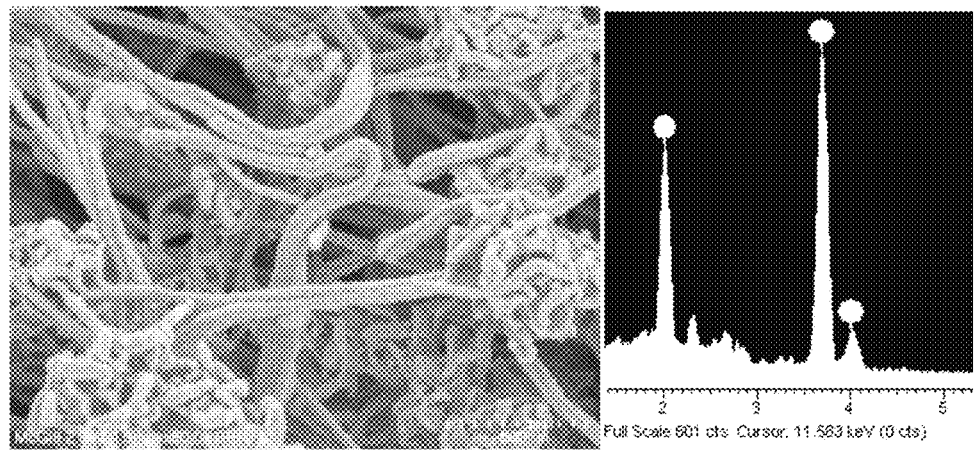
FIG. 7 is a SEM micrograph of an embodiment of the biomaterial of the present invention at day 7 in simulated body fluids, the biomaterial including 10 dry wt % isolated and extracted Cs polypeptides (Example 1)
FIG. 8 is an energy dispersive x-ray diffractogram of an embodiment of the biomaterial of the present invention at day 7 in simulated body fluids, the biomaterial including 10 dry wt % isolated and extracted Cs polypeptides (Example 1)
Figure 9:
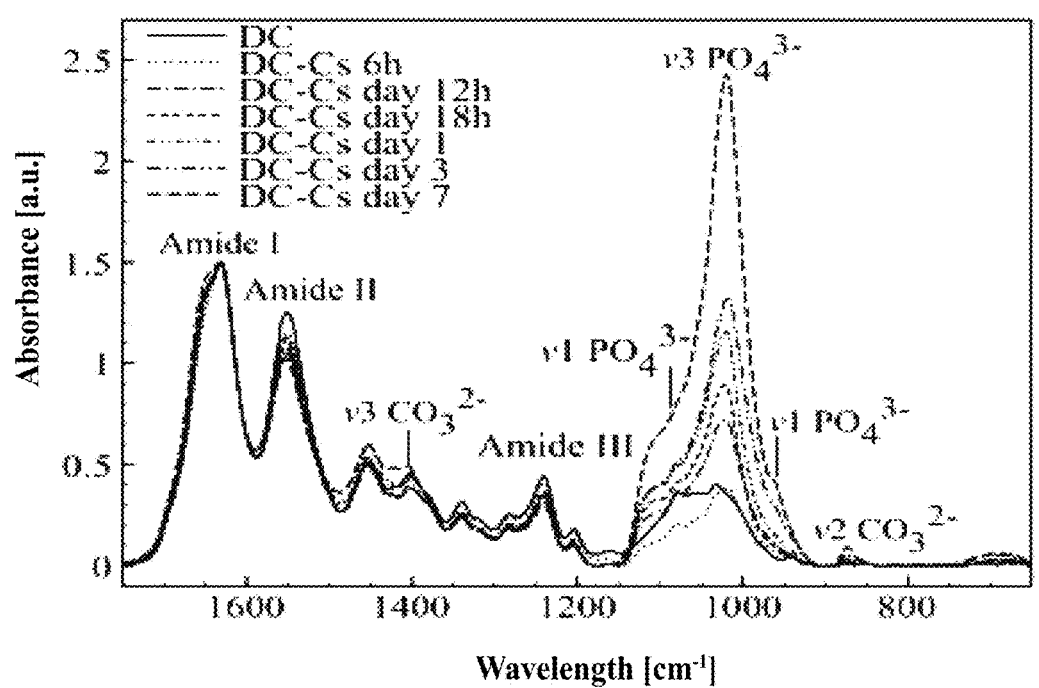
FIG. 9 is ATR-FTIR spectra of embodiments of the biomaterials of the present invention at different times in simulated body fluids compared with a collagen control (DC), the biomaterial including extracted Cs polypeptides (DS-Cp) (Example 1)
Figure 10:
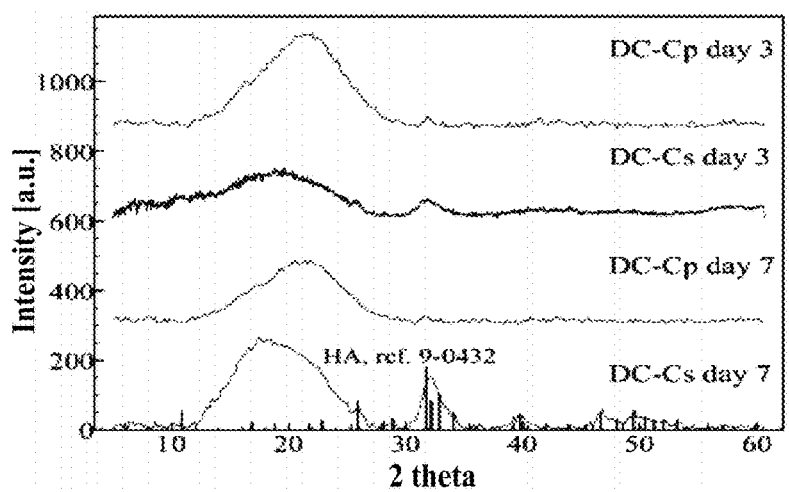
FIG. 10 is diffractogram of embodiments of the biomaterials of the present invention at days 3 and 7 in simulated body fluids compared with a collagen control (DC), the biomaterial including extracted Cp polypeptides (DC-Cp) and Cs polypeptides (DS-Cp) (Example 1)

For biomaterials with isolated and extracted Cs polypeptide particles only, homogenous three-dimensional mineralization occurred in the first day of conditioning in SBF. The extent of mineralization was increased when compared to neat collagen bulk. Nucleation and growth of calcium-phosphate crystals were visible from SEM, microCT, and ATR-FTIR microscopy (FIGS. 7, 8 and 9). Cs polypeptides were no longer visible in the collagenous framework. Without being bound to theory, this was thought to be because they were involved in the nucleation and growth of carbonated hydroxyapatite crystals visible by SEM. EDX analysis confirmed the presence of calcium phosphate crystals at day 7 in SBF. Mineralization, in the form of homogenous bulk formation of carbonated hydroxyapatite in the biomaterial, was detected at days 3 and 7 in SBF by ATR-FTIR microscopy (FIG. 9), and XRD (FIG. 10). Thermogravimetric analysis revealed that the mineralization extent was a function of conditioning time in SBF and reached 57 dry wt % at day 7. Collagen chemical properties were not altered during the mineralization process.

Figure 11:
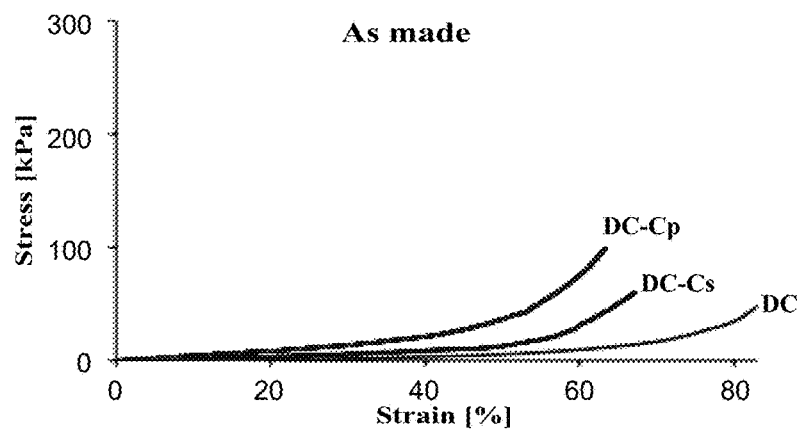
FIG. 11 is a stress-strain graph of embodiments of the dense biomaterials of the present invention (including 10 dry wt % extracted Cs or Cp polypeptides) compared to a dense collagen control under unconfined compressive mechanical testing (Example 1)
Figure 12:
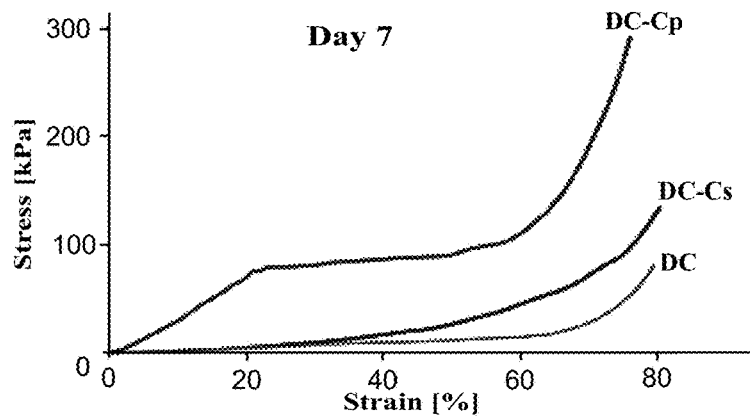
FIG. 12 is a stress-strain graph of embodiments of the dense biomaterials of the present invention (including 10 dry wt % extracted Cs or Cp polypeptide) compared to a dense collagen control under unconfined compressive mechanical testing at day 7 in simulated body fluid (Example 1)

The mechanical properties of the new biomaterials at days 0, 1, 3 and 7 in SBF were assessed by unconfined compression of the rolled biomaterial (FIGS. 11 and 12). A collagen roll with no extracted FDP particles included was used as a control. All the specimen measurements were verified by microCT analysis. As made specimens were characterized after 30 minutes of pre-conditioning in Dulbecco's Modified Eagle Medium (DMEM). Mechanical characterization was achieved on five repeat specimens using an ElectroForce® Biodynamic® Test Instrument 5160 (Bose Corp., MN, USA) with a 15 N load cell. The system was used in displacement control and a rate of 0.01 mms$^{-1}$ was applied. Considering valid the approximation of soft tissues as incompressible material, the compressive strength was calculated as ratio of force measured to resistance area of the cylindrical sample. The strain was computed as percentage of the initial height and the compressive modulus was calculated as the slope of the initial linear portion of the stress-strain curve. The stress-strain relationship showed enhanced mechanical properties due to the incorporation of isolated and extracted FDP particles into a collagenous framework. The improvement in mechanical properties was particularly evident in the biomaterial including only extracted Cp polypeptides (FIG. 11). The incorporation of extracted Cp particles resulted in a higher yield modulus and decreased yield strain. In FIG. 12, for the mineralized biomaterials, stress-strain curves shows a soft to hard tissue transition behaviour occurred in collagen gels hybridized with the extracted Cs polypeptides and due to the homogenous formation of carbonated hydroxyapatite (CHA) within the constructs. In FIG. 12, the biomaterials exhibited higher compression mechanics compared to the control. The compressive modulus of the biomaterials including the extracted Cp fraction was not affected by mineralization, while biomaterials including the extracted Cs fraction exhibited a significant increase in the compressive modulus with time in SBF. Together, these results demonstrated that varying the amount of the extracted Cs and Cp fractions in the new biomaterial can tailor the mechanical properties of the biomaterial. Cp increased the mechanics of the biomaterial. Therefore, a biomaterial with an extracted Cp particle content would be an ideal candidate for soft tissue application for example, non-mineralizing drug delivery. Biomaterials with an extracted Cs particle content exhibited extensive mineralization, when exposed to simulated body fluid, making this biomaterial an ideal candidate for hard tissue application.

Example 2

Collagen Incorporating Different Total Amounts of the Isolated and Extracted FDPs: Effect on the Biomaterial Properties (In Vitro)

In order to assess the range of extracted polypeptide fractions supported by a collagenous material and to retain the beneficial properties of the collagenous material, according to embodiments of the invention, different amounts (<0.1 to >50 dry wt % FDP) of the extracted FDP (Cs alone, Cp alone, and Cp and Cs together) were added to a collagen solution before gelation of the collagen. It was found that below extracted 0.1% FDP, the addition of extracted FDP to collagen was negligible in terms of mineralization and mechanical effects (as set out in Example 1). Furthermore, the incorporation of extracted FDP above 50 dry weight % was hampered by the lack of integration between collagen and FDP at such high concentration of polypeptides in the gel. High integration of the polypeptides with the collagen nanofibrils was achieved, when a 0.1 to 30 dry wt % of FDP was added.

Example 3

Dense Collagen Gels Incorporating Isolated and Extracted Cs and Cp Particles: Effect on Mineralization and Mechanical Properties (In Vitro)

Figure 13:
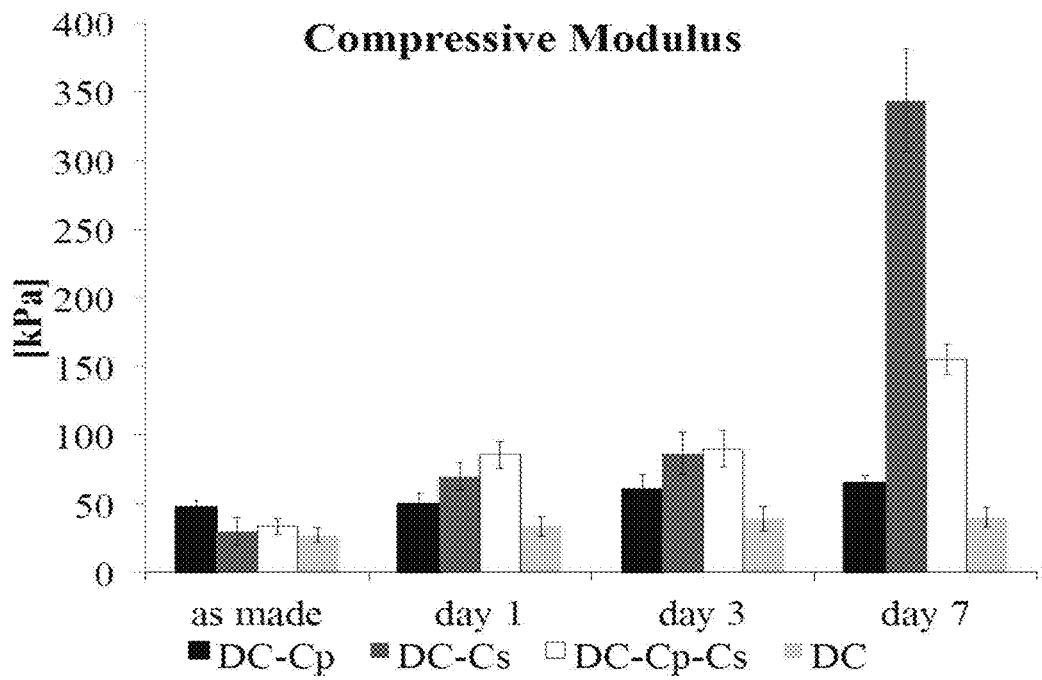
FIG. 13 is a graph showing compressive modulus of dense collagen gel (control) and of embodiments of biomaterials of the present invention (including 10 dry wt % extracted Cs or Cp and 5 dry wt % Cs+5 dry wt % Cp in collagen) as made and at days 3 and 7 in simulated body fluid (Example 3)
Figure 14:
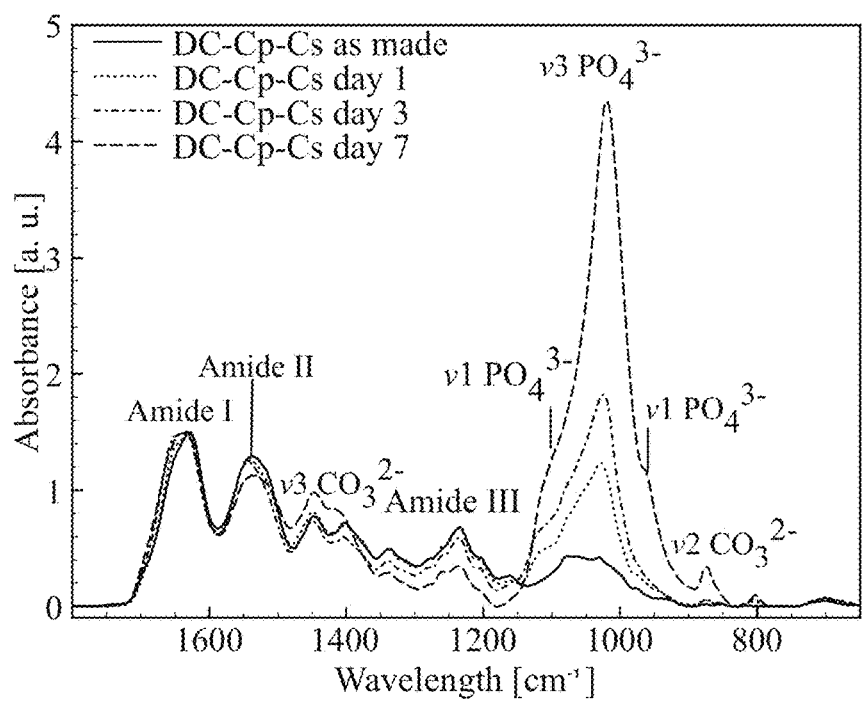
FIG. 14 is ATR-FTIR spectra of embodiments of the biomaterials of the present invention including isolated and extracted Cp and Cs polypeptides in collagen (DC-Cp-Cs) at different times in simulated body fluid (Example 3)
Figure 15:
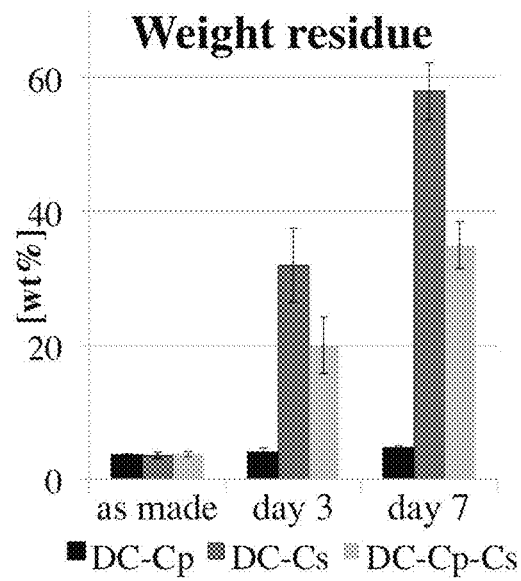
FIG. 15 shows the weight residue of embodiments of biomaterials of the invention (including 10 dry wt % extracted Cs or Cp polypeptide and 5 dry wt % Cs+5 dry wt % Cp in collagen) as made and at days 3 and 7 in simulated body fluid (Example 3)

The method of Example 3 differs from that of Example 1 in that both extracted Cp and Cs polypeptide particles were added to the culture medium or to the collagen solution before self-assembly of the collagen. The extracted Cp and Cs particles were added as 5 and 5 dry wt %, respectively. The incorporation of 5 dry wt % Cp and 5 dry wt % Cs together was found to further tailor the properties of the collagenous gel as well as its chemical and mechanical properties. Mechanical investigation of the dense collagen biomaterial incorporating both extracted Cs and Cp particles (DC-Cp-Cs) showed properties between the dense collagen biomaterial incorporating only Cp (DC-Cp-10 dry wt % Cp) and the dense collagen biomaterial incorporating only Cs (DC-Cs-10 dry wt % Cs) (FIG. 13). DC-Cp-Cs had in fact a lower content of Cp (which is responsible for the increase of the mechanics due to its crystalline structure), with respect to DC-Cp and a higher content with respect to DC-Cs. On the contrary, with time in simulated body fluid (SBF) the lower amount of Cs in DC-Cp-Cs gel, with respect to the DC-Cs one, caused a lower formation of carbonated hydroxyapatite, resulting in lower compressive modulus. However, the compressive modulus of DC-Cp-Cs was higher at day 3 and 7 in SBF when compared to the DC-Cp biomaterial. These results were corroborated by thermogravimetric analysis (TGA). Mineral formation in DC-Cp-Cs was in fact higher than DC-Cp but lower than DC-Cs. FIG. 14 shows changes in the spectra related to the formation of carbonated hydroxyapatite within the collagen framework, as it is visible by the time dependent increase in the absorbance of the phosphate peaks between 1100-900 cm$^{-1}$ and of the carbonate peaks at circa 1420 and 872 cm$^{-1}$. FIG. 15 shows thermogravimetric analysis. Weight residue represents the extent of carbonated hydroxyapatite formed in the constructs.

Example 4

Figure 16:
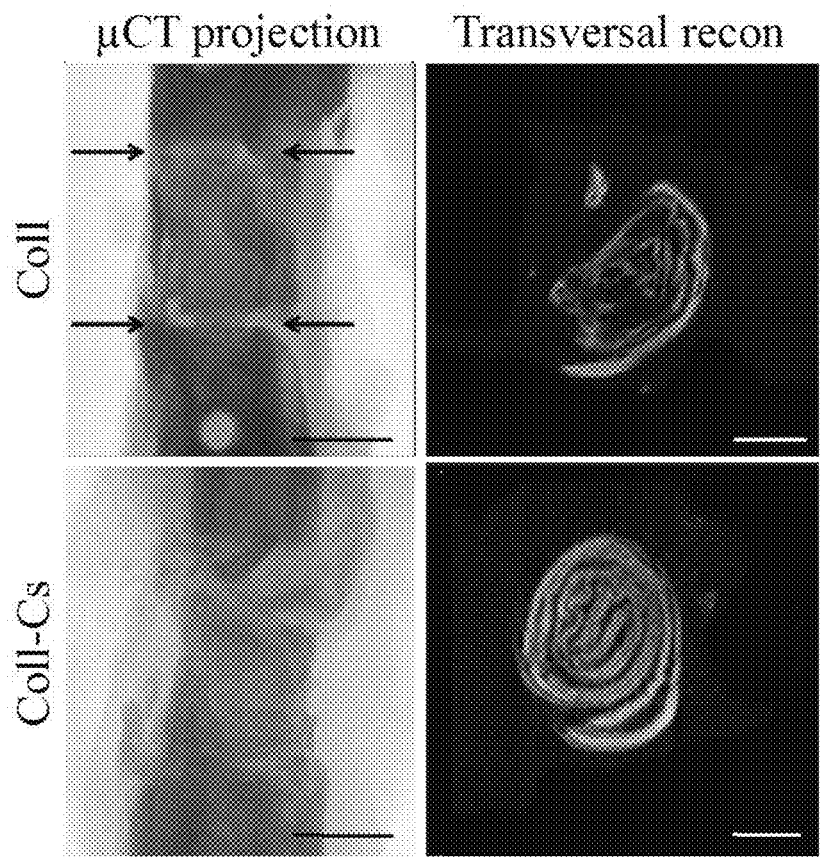
FIG. 16 shows microCT projections and transversal reconstructions of collagen gel (coil) and of embodiments of biomaterials of the invention (including 10 dry wt % extracted Cs in collagen) at 9 weeks of implantation in femoral critical sized defects induced in Sprague Dawley® rats (Example 4)

Dense Collagen Gels Incorporating Isolated and Extracted Cs Particles: Effect on In Vivo Mineralization in an Osseous Site Rod-shaped dense collagen-Cs hybrid gels, according to an embodiment of the present invention, were produced as described in Example 1 by dispersing extracted Cs particles (10 dry wt %) in the collagen solution prior to self-assembly and then applying the plastic compression processing technique. The mineralization of these biomaterials was evaluated by implanting these acellular biomaterials (n=6) in bilateral femoral critical sized defects (l=6 mm) in Sprague Dawley™ Rats (w>350 g) and using dense collagen gels and empty defects as controls. The implants were explanted at 9 weeks and analysed using microCT which showed that the biomaterial underwent homogenous bulk mineralization (FIG. 16). In contrast, the collagen gel controls presented mineralization in the external layer only.

Example 5

Figure 17:
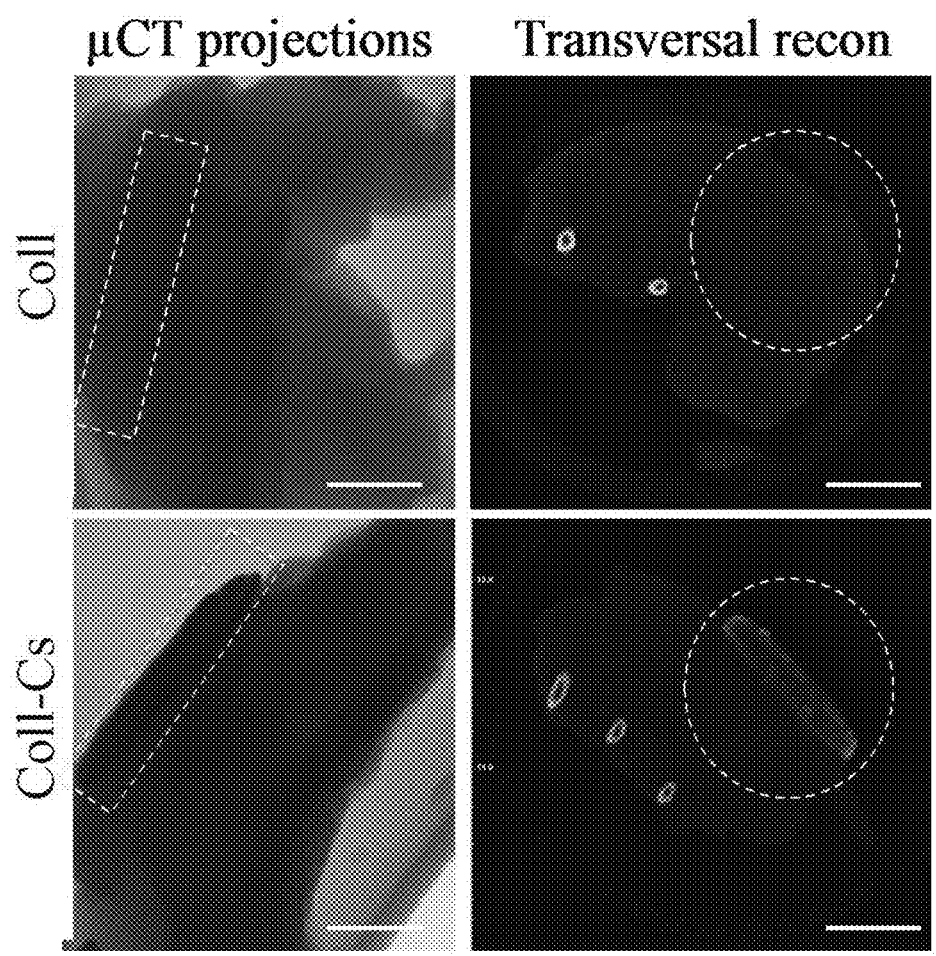
FIG. 17 shows microCT projections and transversal reconstructions of collagen gel (coil) and of embodiments of biomaterials of the present invention (including 10 dry wt % extracted Cs in collagen) at 7 days of subcutaneous implantation in Sprague Dawley® rats (Example 5)

Dense Collagen Gels Incorporating Isolated and Extracted Cs Particles: Effect on In Vivo Mineralization in a Non-Osseous Site Disk shaped dense collagen-Cs hybrid gels, according to an embodiment of the present invention, were produced as described in Example 1 by dispersing extracted Cs particles (10 dry wt %) in the collagen solution prior to self-assembly and then applying the plastic compression fabrication technique. Sprague Dawley™ rats (w>350 g) received 2 subcutaneous implantations on either side of the spine just behind the shoulder blades. Each rat received two treatments: control dense collagen gels, and dense collagen-Cs gels according to an embodiment of the present invention. After 7 days, tissue was harvested for analysis and the formation of bone was observed through microCT measurements (FIG. 17). The control collagen samples did not mineralize, as they were not distinguishable from the surrounding soft tissue (FIG. 17, first row). In contrast, the collagen-Cs biomaterials underwent mineralization as they appear in lighter grey than the surrounding soft tissue in transversal microCT reconstruction (FIG. 17, second row). Very light grey circles in the transversal reconstructions represent the ribs in the surrounding of the implants

Example 6

Cell-Seeded Collagen Gels Incorporating Isolated and Extracted Cs Particles: Osteogenicity Dense collagen-Cs hybrid gels, according to an embodiment of the present invention, were produced as described in Example 1, using 10 dry wt % of extracted Cs particles. It was found that the resulting biomaterials can be homogenously seeded with different types of cells (e.g. osteoblasts or stem cells as MSCs, cell density: 0.5 k-1000 k cells/ml of collagen solution). In this example, mouse-mesenchymal stem cells (m-MSCs) were seeded at the point of collagen self-assembly (gelling). The osteogenic potential of the cell seeded collagen-Cs biomaterial was investigated in osteogenic medium. Cell viability was investigated through maximum intensity projections of calcein-AM labelled cell cytoplasm and EtBr-1 nucleus binding throughout the radius of the constructs as a function of time in culture (days 1, 7, 14, and 21). Cell metabolic activity was evaluated through Alamar Blue® assay. Osteoblastic differentiation was evaluated through expression of osteoblastic genes as alkaline phosphatase (ALP), runt-related transcription factor 2 (Runx2), and osteopontin (OPN). Qualitatively, Von Kossa staining of histological sections of the gels was used to assess the distribution of the mineral formation. FTIR was also used to evaluate the mineral phase formed.

Figure 18:
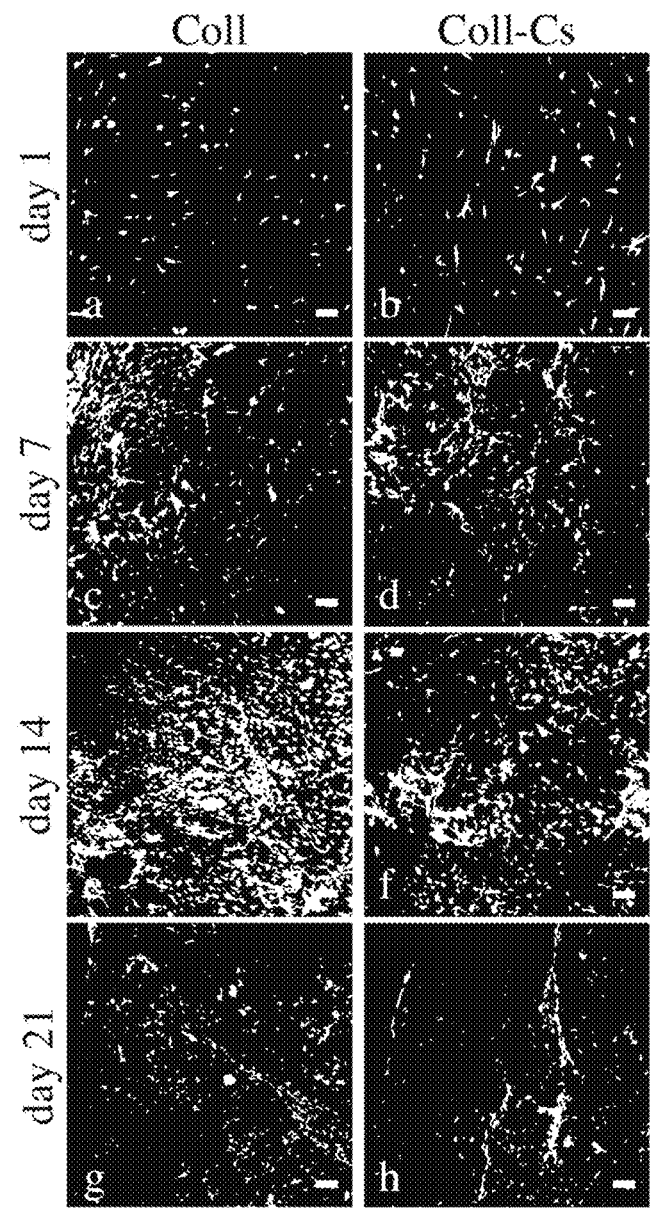
FIG. 18 shows confocal laser microscopy images of mouse mesenchymal stem cells seeded in collagen gel (coil) and in embodiments of biomaterials of the present invention (including 10 dry wt % extracted Cs in collagen) at days 1, 7, 14 and 21 in osteogenic medium (Example 6)
Figure 19A:
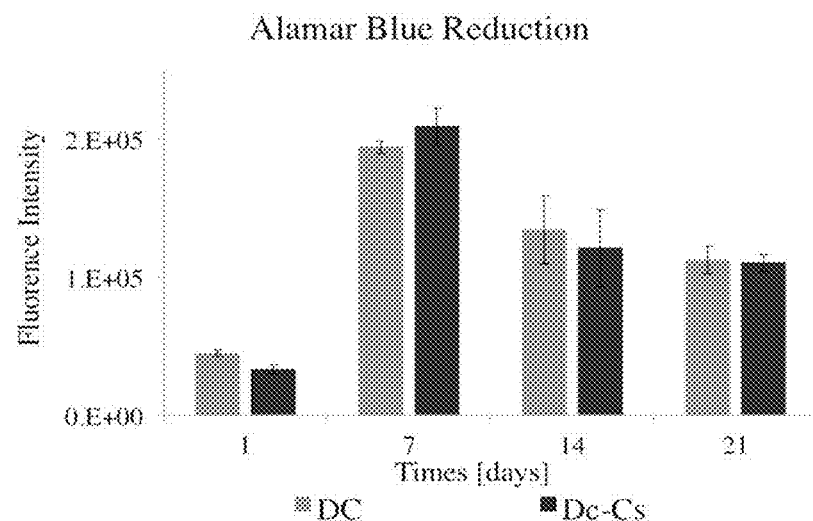
FIG. 19 shows metabolic activity of mouse mesenchymal stem cells (m-MSCs) seeded in collagen gel (coll) and in embodiments of a biomaterial of the present invention (including 10 dry wt % extracted Cs in collagen) in terms of (a) Alamar Blue® reduction at days 1, 7, 14 and 21 culture in osteogenic medium, and (b) alkaline phosphate (ALP), Runt-related transcription factor 2 (Runx2), and osteopontin (OPN) expression of the seeded m-MSCs at day 21 of culture (Example 6)
Figure 19B:
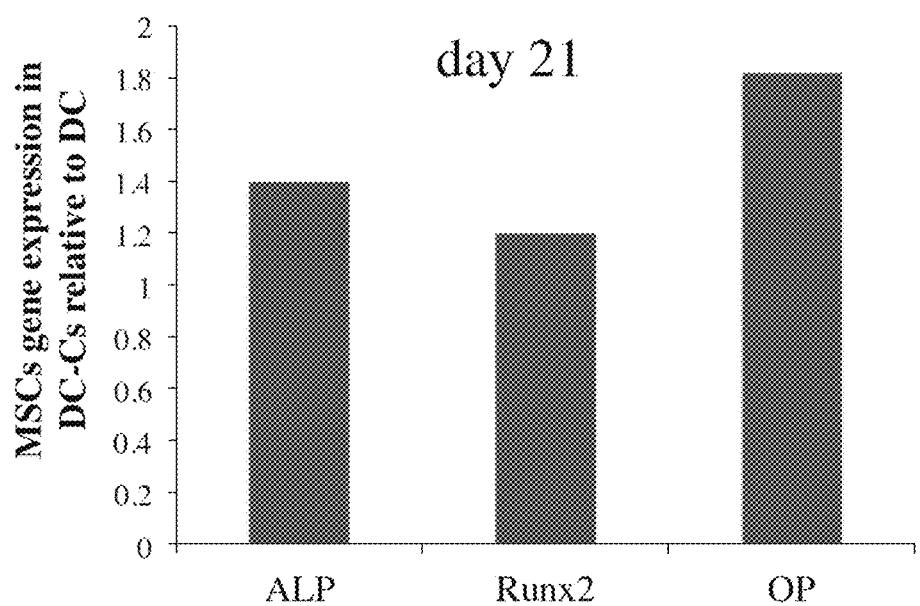
Figure 20:
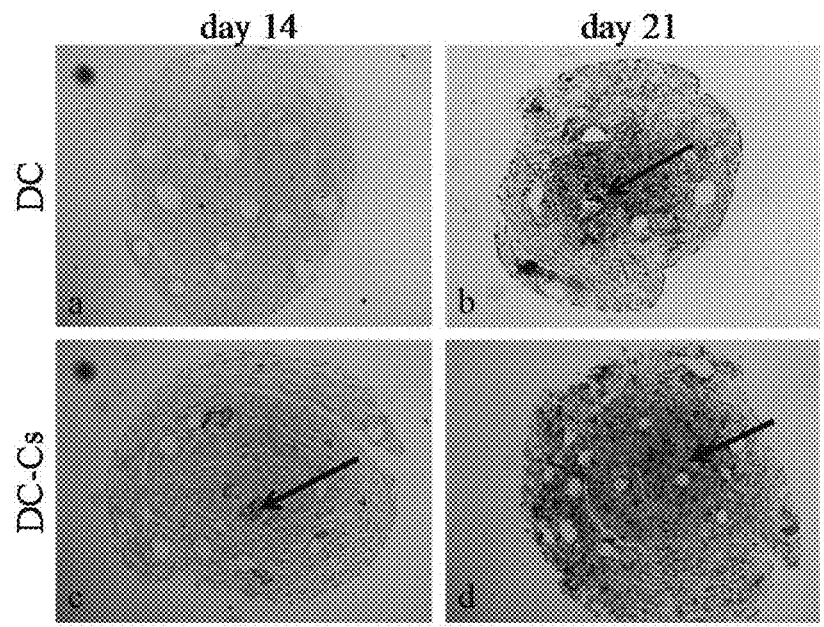
FIG. 20 shows Von Kossa staining for calcium phosphate of representative histological sections of m-MSC seeded in collagen gel (coil) and in embodiments of a biomaterial of the invention (including 10 dry wt % extracted Cs in collagen) at days 14 and 21 of culture (Example 6)
Figure 21:
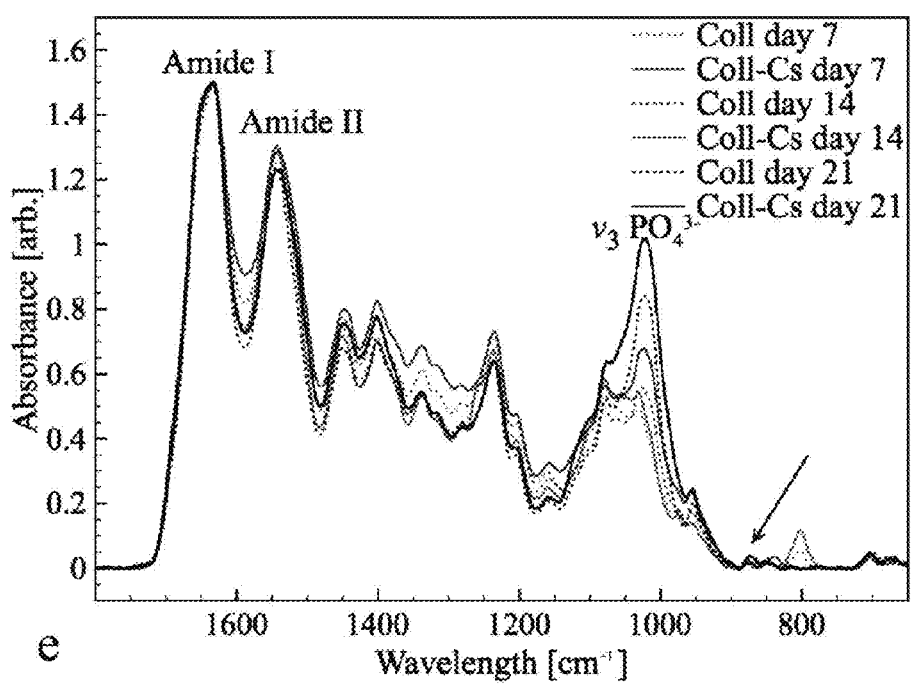
FIG. 21 shows ATR-FTIR spectra of m-MSC seeded in collagen gel (coil) and in embodiments of a biomaterial of the invention (including 10 dry wt % extracted Cs in collagen) at days 7, 14 and 21 of culture (Example 6)

The left column of FIG. 18 shows the results obtained for collagen gels, used as control. The right column of FIG. 18 shows the results obtained for the cell seeded collagen-Cs gels, according to an embodiment of the present invention. m-MSCs attachment to the collagenous framework was indicated already at day 1. Progressively, at days 7, 14 and 21 there was an increase in cell number in both gel environments, an indication of the excellent cytocompatibility of the extracted Cs polypeptides. In addition, the metabolic activity of the m-MSCs seeded in collagen and collagen-Cs resulted not statistically different (p>0.05) for all the time of culture (21 days), as from Alamar Blue reduction results (FIG. 19a). Surprisingly, mMSCs seeded collagen-Cs up-regulated the expression of osteoblastic genes such as ALP, Runx2, and OPN when compared to the one cultured in the control collagen gels, indicating a remarkable accelerated osteoblastic differentiation (FIG. 19b). Moreover, there was a substantial increase in the mineralization of the collagens (FIG. 20). Von Kossa staining for calcium phosphate of representative histological sections of m-MSC seeded in collagen and collagen-Cs biomaterial rolls were taken at days 14 and 21 in culture. Brown spots represent cells while darker regions represent mineralized matrix (FIG. 20 a to d). Mineralization nodules were present in the collagen-Cs biomaterial but not in the control collagen gels at day 14 in culture, indicating accelerated mineralization of the hybrid gels. In addition, while both collagen and collagen-Cs gels were positively stained at day 21, the mineralization of the hybrid structures was more homogenous and present throughout the thickness of the gels. ATR-FTIR spectra of the m-MSCs seeded control collagen and collagen-Cs gels at days 14 and 21 in culture are presented in FIG. 21. An increase in the absorbance of the $v_3$ $PO_4^{3-}$ and $v_2$ $CO_3^{2-}$ bands at 1018 and 872 $cm^{-1}$ (black arrow), respectively, suggested the formation of carbonated hydroxyapatite. The higher absorbance of the $v_3$ $PO_4^{3-}$ vibration at days 7, 14 and 21 indicates an accelerated mineralization of the collagen-Cs biomaterials when compared to the cell seeded collagen controls.

Example 7

Figure 22:
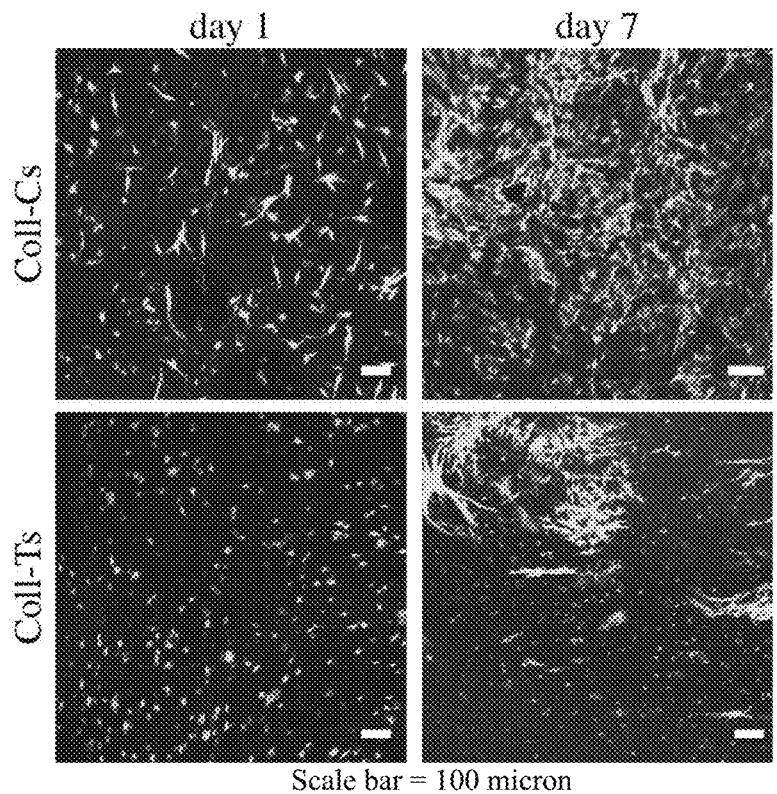
FIG. 22 shows confocal laser microscopy images of m-MSCs seeded in collagen gel (coil) and of a biomaterial made with 10 dry wt % Ts and collagen at days 1, 7, in osteogenic medium (Example 7)

Cell-Seeded Collagen Gels Incorporating Isolated and Extracted Ts Particles: Cell Viability Ts is the soluble fraction of silk fibroin obtained through trypsinization of the protein. Ts fraction was extracted following the same experimental procedure described in Example 1 for Cs, but using Trypsin as protease instead of α-chymotrypsin. Cell seeded rod-shaped dense collagen-Ts hybrid gels were produced by dispersing m-MSCs and extracted Ts particles (10 dry wt %) in the collagen solution prior to self-assembly and then applying the plastic compression fabrication technique as described in Examples 1 and 6. Confocal scanning laser microscopy was used to investigate cell viability in collagen-Cs and collagen-Ts hybrid systems through maximum intensity projections of calcein-AM labelled cell cytoplasm and EtBr-1 nucleus binding throughout the radius of the constructs at days 1 and 7 in culture (FIG. 22). The upper row shows Coll-Cs hybrid rolls at days 1 and 7 in culture, and the lower row shows Coll-Ts hybrid rolls at days 1 and 7 in culture. At day 1, m-MSCs were well adherent to the Coll-Cs scaffold, while in Coll-Ts m-MSCs maintained the round shape, typical of the non-adherent status. At day 7 there was an increase in cell number for Coll-Cs gels. On the contrary, m-MSCs cultured in Coll-Ts gels resulted in a suffering status, as they did not proliferate and were not well attached to the collagenous matrix. The ability of Cs to not only maintain cell viability but also steer the osteoblastic lineage of stem cells was confirmed by comparing Cs to another polypeptide fraction derived from fibroin, Ts. Ts appeared to negatively affect the m-MSCs seeded in the biomaterial, and can be considered as cytotoxic.

Example 8

Collagen Gels Incorporating Isolated and Extracted Cs Particles: Injectability Injectable h-MSCs seeded Coll-Cs gels were prepared according to an embodiment of the present invention by mixing 3.2 ml of type I collagen solution with 0.8 ml of 10 times concentrated Dulbecco Modified Eagle Medium (10× DMEM), 30 μl of 5M NaOH and h-MSCs (circa. 5 k-1000 k cells/ml of collagen solution, preferably 2×10$^5$ cells/ml). The solution (4 ml) was then placed in a glass syringe and set to start fibrillogenesis at 4° C. for 35 minutes. The partially gelled biomaterial was then injected through a metal needle (Ø=0.05-1.5 mm) to an in vivo site. The injected biomaterial continued its self-assembly in vivo. The cells remained viable after injecting. It will be appreciated that different types of cells can be delivered in this way (e.g. osteoblasts or stem cells). By injecting the biomaterial, a less invasive procedure is obtained. Once injected, the biomaterial can further gel in situ, fill awkward shapes, and allow for direct contact between transplanted cells contained in the biomaterial and the host tissue. A range of extracted FDP of <0.1 to >50 dry wt %, with a preference for 10 wt % may be used.

Example 9

Characterization of Isolated and Extracted Cs and Cp

Cs and Cp fractions were isolated and extracted from silk fibroin as described in Example 1. Specifically, a ~1% w/v silk fibroin (SF) was prepared by dissolving 1.7 g of SF-f with 50 ml of saturated aqueous LiBr, at 60° C., for 3 hrs. After dilution with 50 ml of distilled water, the solution was filtered, and extensively dialyzed against water until complete removal of salt. SF concentration was determined spectrophotometrically at 280 nm ($A_{1\%;1cm}$=11.3). Preparation of chymotryptic fractions of SF: a 1% w/v SF was diluted 1:1 with aqueous ammonium carbonate 0.1M, to which α-chymotrypsin, previously dissolved in a small volume of HCl 1 mM, was added. The enzyme-to-substrate ratio was 1:100. The solution was incubated at 37° C. for 24 hrs, during which a gelatinous precipitate formed. The precipitate (Cp fraction) was recovered by centrifugation, washed twice with water and then freeze-dried. Supernatant was pooled to washings and freeze-dried to recover soluble peptides (Cs fraction).
Amino acid analysis: after acid hydrolysis with 6N HCl, at 105° C. for 24 hrs, under vacuum, the free amino acids were determined by HPLC according to the AccQ-Tag Method (Waters). Samples were analyzed in duplicate. External standard calibration was used (Amino Acid Standard H, Pierce). Results are presented in Table 1.

TABLE 1

| Amino acid composition | | | | |
|---|---|---|---|---|
| Amino Acid (mol %) | Silk Fibroin | Silk Sericin | Cs fraction | Cp fraction |
| Asp | 1.6 | 17.0 | 4.5 | 0.4 |
| Ser | 11.3 | 34.8 | 9.2 | 11.8 |
| Glu | 1.2 | 4.1 | 3.1 | 0.3 |
| Gly | 45.9 | 15.8 | 36.9 | 49.1 |
| His | 0.3 | 1.4 | 0.5 | 0.0 |
| Arg | 0.5 | 2.5 | 1.3 | 0.1 |
| Thr | 0.9 | 6.9 | 1.9 | 0.5 |
| Ala | 28.6 | 4.7 | 24.0 | 32.0 |
| Pro | 0.4 | 0.7 | 1.0 | 0.1 |
| Cys | 0.0 | 0.3 | 0.0 | 0.0 |
| Tyr | 5.1 | 3.4 | 7.5 | 3.7 |
| Val | 2.1 | 3.2 | 4.2 | 1.1 |
| Met | 0.1 | 0.0 | 0.3 | 0.0 |
| Lys | 0.3 | 2.7 | 0.9 | 0.1 |
| Ile | 0.6 | 0.7 | 1.6 | 0.2 |
| Leu | 0.5 | 1.3 | 1.7 | 0.1 |
| Phe | 0.7 | 0.4 | 1.5 | 0.3 |

Typical features of the amino acid composition of silk proteins are:

Silk Fibroin (SF): high content of Gly, Ala, and Ser, which total about 85 mol %; Tyr accounts for about 5 mol %; acidic and basic amino acids total about 2.7 and 1.1 mol %, respectively; this characteristic amino acidic pattern results from the contribution of at least three polypeptides:

- the heavy (H) chain, 350 kDa (native), which contribute for about 90% of the total weight of SF; its sequence is of the poly(Ala-Gly) type, because-(Gly-Ala)$_n$- repeats form the largest part of the primary structure;
- the light (L) chain and P25, 25 kDa each (native); these two polypeptides are more heterogeneous in composition;
- H and L chains are linked by a disulphide bridge; the H:L:P25 molar ratio is 6:6:1;

Silk Sericin (SS): native SS is composed of 5-6 polypeptides, widely ranging in molecular weight (40-400 kDa); their primary structure is characterized by high content of Ser (from 30 to 40 mol % in the individual polypeptides), Asp (16-17 mol %), and Thr (~7 mol %). SS are globular proteins which stick on the surface of the fibrous SF component in a denatured state owing to the physical and mechanical stresses occurring during silk spinning.

Silk fibroin peptides were isolated by subjecting a SF-aqueous solution to chymotryptic digestion. Cleavage specificity of α-chymotrypsin is as follows: Trp, Tyr, Phe (high specificity), Leu, Met, His (low specificity). Considering the primary structure of H and L chains of SF (known from the literature), we may expect a high number of cleavage sites, i.e.: H chain: 317 (hi), 332 (lo), and L chain: 21 (hi), 47 (lo) (Table 2). Chymotryptic digestion of SF results in two peptide fractions, each one accounting for about 50 w % of the starting material. One fraction is water soluble (Cs) and is formed by SF peptides belonging to the amorphous regions of the fibre. Their amino acid composition is enriched in residues with bulky and polar side chains, though Gly and Ala still remain the most abundant. The molecular weight of these peptides is highly variable, ranging from 2 to 10 kDa. The other fraction (Cp), which precipitates during enzymatic digestion, is formed by the most hydrophobic peptides mainly comprising the repetitive -(Ala-Gly)$_n$- sequences characteristic of the crystalline regions of the fibre.

TABLE 2

Enzymatic cleavage of Silk Fibroin Heavy chain by α-chymotrypsin.

| Enzyme | No. of cleavages | Position of cleavage sites |
|---|---|---|
| α-Chymotrypsin | 317 | 6 15 18 26 30 31 84 115 123 129 135 141 145 171 189 201 213 225 237 249 261 273 311 323 333 341 363 369 385 393 397 405 409 483 491 537 545 553 561 631 639 643 651 678 681 687 693 695 697 701 741 749 753 761 851 859 929 937 941 949 1031 1039 1043 1051 1115 1123 1127 1135 1193 1197 1205 1232 1235 1241 1244 1246 1248 1254 1286 1294 1298 1306 1370 1374 1382 1440 1448 1452 1460 1518 1522 1530 1588 1596 1600 1608 1635 1638 1644 1647 1649 1651 1657 1691 1695 1703 1779 1787 1791 1799 1826 1829 1835 1838 1840 1842 1848 1894 1902 1906 1914 1990 1998 2062 2070 2074 2082 2104 2112 2116 2124 2212 2220 2224 2232 2266 2270 2297 2300 2306 2309 2311 2313 2319 2347 2355 2359 2367 2389 2397 2407 2447 2451 2459 2505 2513 2517 2525 2589 2616 2619 2625 2628 2630 2632 2638 2672 2680 2684 2692 2744 2796 2804 2808 2816 2888 2892 2900 2956 2964 2968 2976 3084 3092 3096 3104 3164 3168 3176 3184 3192 3228 3255 3258 3264 3267 3269 3271 3277 3311 3319 3359 3411 3415 3423 3427 3435 3487 3495 3499 3507 3579 3583 3591 3647 3655 3659 3667 3747 3755 3759 3767 3794 3797 3803 3806 3808 3810 3816 3838 3842 3850 3858 3866 3908 3912 3920 3928 3936 3988 3992 4000 4008 4016 4094 4102 4106 4113 4159 4186 4189 4194 4197 4199 4201 4207 4229 4237 4241 4249 4323 4331 4335 4343 4413 4417 4425 4433 4441 4501 4505 4532 4535 4541 4544 4546 4548 4554 4576 4584 4588 4596 4654 4658 4666 4674 4682 4754 4758 4766 4774 4782 4852 4860 4928 4932 4940 4946 4950 4958 5008 5016 5024 5072 5114 5139 5142 5148 5154 5156 5158 5164 5208 5214 5233 5235 5255 |

Figure 23A:
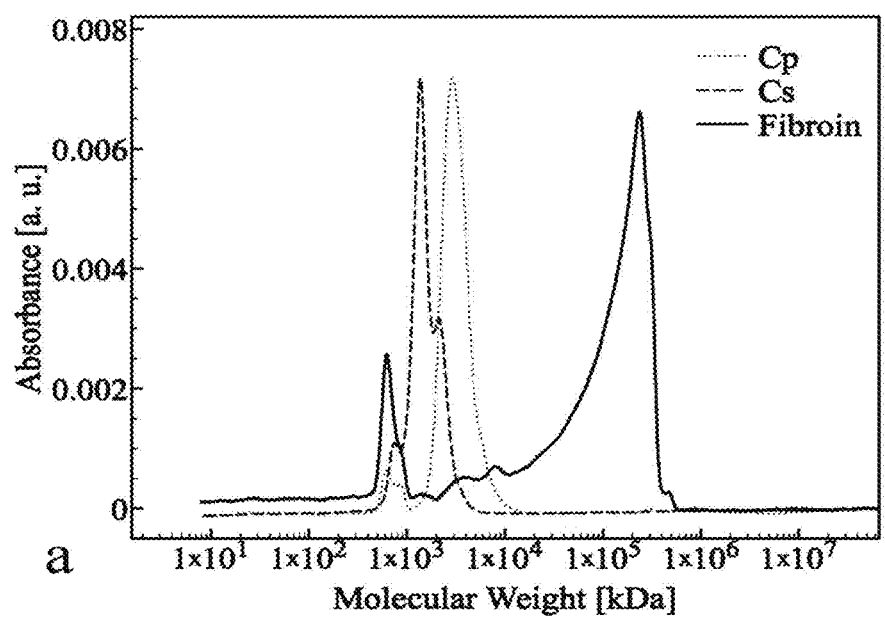
FIG. 23a is high performance size exclusion chromatography profiles of silk fibroin and of isolated and extracted Cp and Cs fractions indicating their molecular weight (Example 9)
Figure 23B:
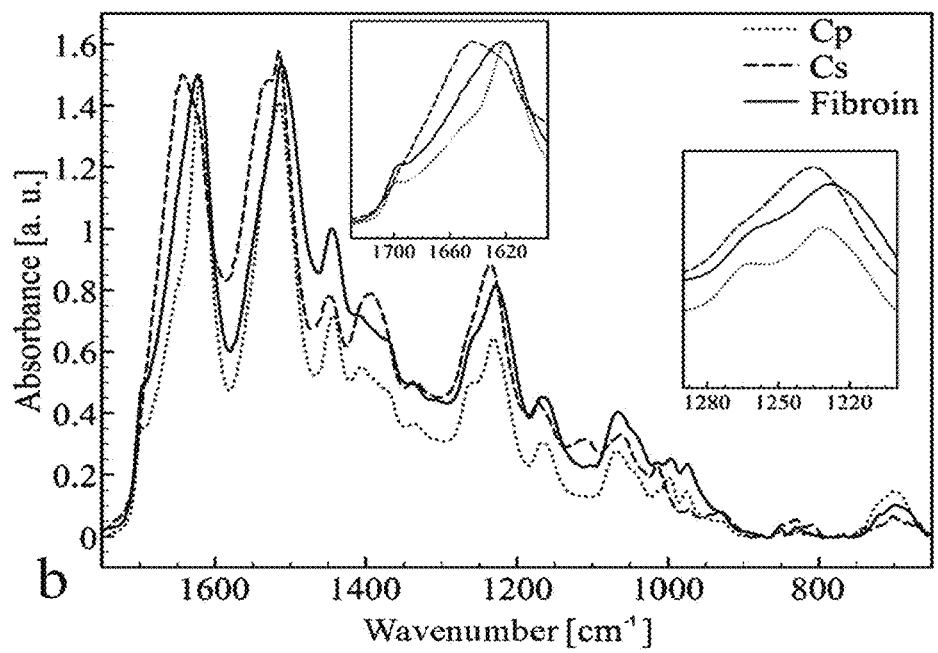
FIG. 23b is a ATR-FTIR spectra of silk fibroin and of isolated and extracted Cp and Cs fractions indicating their molecular weight (Example 9)

FIG. 23 shows the physico-chemical characterization of silk fibre and its extracted Cp and Cs fractions. a) High performance size exclusion chromatography profiles of SF and of α-chymotryptic Cp and Cs fractions of the protein indicating their molecular weight; b) ATR-FTIR spectra of SF, Cp and Cs. The left and right insets show a close-up of the amide I and III resonances, respectively. Spectra of SF and Cp fragments confirmed their antiparallel β-sheet structure (amide I absorbance at 1692 and 1621 cm$^{-1}$), whereas the spectrum of Cs fragments was compatible with an amorphous polypeptide, with few β-sheet structures.

Example 10

Isolated and Extracted Cs and Cp Alone: Mineralization Behaviour in SBF

Figure 24:
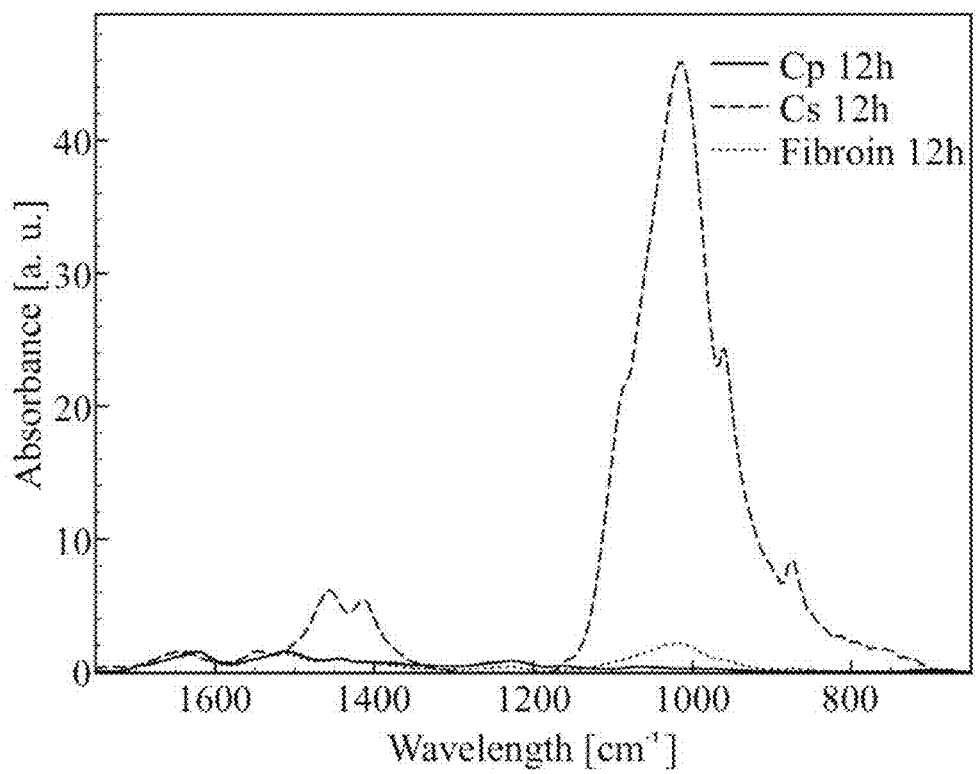
FIG. 24 is ATR-FTIR spectra of silk fibroin and extracted Cp and Cs at 12 hours in simulated body fluid (Example 10).

Cs polypeptide fractions and Cp polypeptide fractions were isolated from silk fibroin and extracted as previously described (Example 1). The extracted polypeptide fractions were placed in simulated body fluid (SBF) for 12 hours in order to evaluate their mineralization. As can be seen from the ATR-FTIR spectra of FIG. 24, Cs templated the formation of carbonated apatite as their spectra were characterized by strong carbonate (1440 and 872 cm$^{-1}$) and phosphate (1078, 1035 and 957 cm$^{-1}$) absorptions. Silk fibroin and extracted Cp exhibited only minor or no indications of apatite formation, respectively. The left and right insets show a close-up of the amide I and III resonances, respectively.

It should be appreciated that the invention is not limited to the particular embodiments described and illustrated herein but includes all modifications and variations falling within the scope of the invention as defined in the appended claims.

The invention claimed is:

1. A biomaterial comprising a chymotryptically isolated and extracted polypeptide fraction of fibroin incorporated in a hydrogel or a hydrogel precursor, the chymotryptically isolated and extracted polypeptide fraction consisting of a soluble fraction Cs.

2. The biomaterial of claim 1, wherein the soluble fraction Cs is incorporated in a hydrogel precursor and the biomaterial can gel in situ.

3. The biomaterial of claim 2, wherein the hydrogel precursor is a collagen solution.

4. The biomaterial of claim 1, wherein the soluble fraction Cs is incorporated in a hydrogel and the biomaterial is substantially solid or gel-like and implantable.

5. The biomaterial of claim 4, wherein the hydrogel is a collagenous material.

6. The biomaterial of claim 4, wherein the implantable biomaterial is a flat or a rolled sheet, sponge or film.

7. The biomaterial of claim 1, wherein the isolated and extracted polypeptide fraction is incorporated in the hydrogel or hydrogel precursor in the range of about 0.1 to about 50 dry wt %, about 0.1 to about 30 dry wt %, about 5 to about 10 dry wt %, or about 10 dry wt %.

8. The biomaterial of claim 1, wherein the Cs content is less than or equal to about 30 dry wt % Cs in a collagen hydrogel or collagen hydrogel precursor.

9. The biomaterial of claim 1, wherein the isolated and extracted polypeptide fraction is in the form of particles.

10. The biomaterial of claim 1, wherein the fibroin originates from a silk worm or a spider.

11. The biomaterial of claim 1, further comprising cells, drug molecules, therapeutic agents, particles or bioactive agents.

12. A method for constructing, regenerating, repairing, replacing or augmenting hard tissue in a subject, comprising administering the biomaterial of claim 1, wherein the biomaterial is administered as an in vivo construct, as a coating material, or as a cell, molecule or particle delivery medium, such that the hard tissue is constructed, regenerated, repaired, replaced or augmented in the subject.

13. A method for promoting mineralization, osteoinduction, osteoconduction or osteogenesis in a subject, comprising administering the biomaterial of claim 1, such that mineralization, osteoinduction, osteoconduction or osteogenesis is promoted in the subject.

14. A method for promoting mineralization, osteoinduction, osteoconduction or osteogenesis in a subject, comprising administering an isolated and extracted polypeptide fraction of fibroin, Cs, wherein the isolated and extracted polypeptide fraction Cs is isolated by a-chymotrypsin digestion of the fibroin and is separated from a polypeptide fraction Cp, such that mineralization, osteoinduction, osteoconduction or osteogenesis is promoted in the subject.

15. The method of claim 14, wherein the isolated and extracted polypeptide fraction is incorporated in a biomaterial.

16. The method of claim 14, wherein the isolated and extracted polypeptide fraction of fibroin is administered as an in vitro or in vivo construct, as a coating material, or as a cell, molecule or particle delivery medium.

17. The method of claim 14, wherein the subject is a mammal and the isolated and extracted polypeptide fraction of fibroin is administered in a therapeutically effective amount to treat a bone or a tooth defect.

18. The method of claim 14, wherein the fibroin originates from a silk worm or a spider.

19. The method of claim 14, further comprising administering cells, drug molecules, therapeutic agents, particles or bioactive agents with the isolated and extracted polypeptide fraction of fibroin to the subject.

20. The method of claim 14, wherein the isolated and extracted polypeptide fraction is in the form of particles.

* * * * *

UNITED STATES PATENT AND TRADEMARK OFFICE
CERTIFICATE OF CORRECTION

| | | |
|---|---|---|
| PATENT NO. | : 9,993,525 B2 | Page 1 of 1 |
| APPLICATION NO. | : 14/002070 | |
| DATED | : June 12, 2018 | |
| INVENTOR(S) | : Showan N. Nazhat et al. | |

It is certified that error appears in the above-identified patent and that said Letters Patent is hereby corrected as shown below:

On the Title Page

Item (73) the Assignee should read "THE ROYAL INSTITUTION FOR THE ADVANCEMENT OF LEARNING/MCGILL UNIVERSITY, Montreal, QC" and not "THE ROYAL INSTITUTION FOR THE ADVANCEMENT OF LEARNING, Montreal, QC; MCGILL UNIVERSITY, Montreal, QC"

Signed and Sealed this
Twentieth Day of November, 2018

Andrei Iancu
*Director of the United States Patent and Trademark Office*